United States Patent
Cooper et al.

(10) Patent No.: US 10,898,281 B2
(45) Date of Patent: *Jan. 26, 2021

(54) MODULAR MANIPULATOR SUPPORT FOR ROBOTIC SURGERY

(71) Applicant: Intuitive Surgical Operations, Inc., Sunnyvale, CA (US)

(72) Inventors: Thomas G. Cooper, Menlo Park, CA (US); Stephen J. Blumenkranz, Los Altos Hills, CA (US); Gary S. Guthart, Los Altos, CA (US); David J. Rosa, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 261 days.

This patent is subject to a terminal disclaimer.

(21) Appl. No.: 15/978,357

(22) Filed: May 14, 2018

(65) Prior Publication Data

US 2018/0256270 A1    Sep. 13, 2018

Related U.S. Application Data

(60) Continuation of application No. 14/271,763, filed on May 7, 2014, now Pat. No. 9,968,405, which is a
(Continued)

(51) Int. Cl.
*A61B 34/30* (2016.01)
*A61B 90/10* (2016.01)
(Continued)

(52) U.S. Cl.
CPC ............. *A61B 34/30* (2016.02); *A61B 34/37* (2016.02); *A61B 34/71* (2016.02); *A61B 90/10* (2016.02);
(Continued)

(58) Field of Classification Search
CPC .............. A61B 34/37; A61B 2034/304; A61B 2090/506; A61B 2090/508; A61B 90/10
See application file for complete search history.

(56) References Cited

U.S. PATENT DOCUMENTS

| 906,874 A | 12/1908 | Hallowell |
| 1,638,938 A | 8/1927 | Koenigkramer |

(Continued)

FOREIGN PATENT DOCUMENTS

| CN | 1155833 A | 7/1997 |
| CN | 1243690 A | 2/2000 |

(Continued)

OTHER PUBLICATIONS

European Search Report for Application No. EP10182807, dated Nov. 9, 2012, 7 pages.
(Continued)

*Primary Examiner* — Kaitlyn E Smith

(57) ABSTRACT

A robotic surgery system comprises a mounting base, a plurality of surgical instruments, and an articulate support assembly. Each instrument is insertable into a patient through an associated minimally invasive aperture to a desired internal surgical site. The articulate support assembly movably supports the instruments relative to the base. The support generally comprises an orienting platform, a platform linkage movably supporting the orienting platform relative to the base, and a plurality of manipulators mounted to the orienting platform, wherein each manipulator movably supports an associated instrument.

16 Claims, 22 Drawing Sheets

Related U.S. Application Data division of application No. 13/706,738, filed on Dec. 6, 2012, now Pat. No. 9,023,060, which is a division of application No. 12/362,299, filed on Jan. 29, 2009, now Pat. No. 8,348,931, which is a continuation of application No. 11/043,688, filed on Jan. 24, 2005, now Pat. No. 7,763,015.

(51) Int. Cl.
| | | |
|---|---|---|
| *A61B 34/00* | (2016.01) | |
| *A61B 34/37* | (2016.01) | |
| *A61B 17/00* | (2006.01) | |
| *A61B 90/50* | (2016.01) | |
| *A61B 90/00* | (2016.01) | |

(52) U.S. Cl.
CPC ... *A61B 90/361* (2016.02); *A61B 2017/00477* (2013.01); *A61B 2034/304* (2016.02); *A61B 2034/305* (2016.02); *A61B 2090/506* (2016.02); *Y10S 901/09* (2013.01); *Y10S 901/14* (2013.01); *Y10S 901/15* (2013.01); *Y10S 901/16* (2013.01); *Y10S 901/17* (2013.01); *Y10S 901/18* (2013.01)

(56) References Cited

U.S. PATENT DOCUMENTS

| | | |
|---|---|---|
| 1,644,231 A | 10/1927 | Bosworth |
| 2,076,446 A | 4/1937 | Carwardine |
| 2,090,439 A | 8/1937 | Carwardine |
| 2,131,693 A | 9/1938 | Smith |
| 2,287,577 A | 6/1942 | Stava |
| 2,416,910 A | 3/1947 | Crosby et al. |
| 2,547,532 A | 4/1951 | Mendelsohn |
| 2,665,102 A | 1/1954 | Perbal |
| 2,700,524 A | 1/1955 | Lauterbach |
| 2,833,504 A | 5/1958 | Sacksteder |
| 2,834,568 A | 5/1958 | Foster |
| 2,866,101 A | 12/1958 | Wagner et al. |
| 2,910,335 A | 10/1959 | Wales |
| 2,941,776 A | 6/1960 | Lauterbach |
| 3,000,606 A | 9/1961 | Storm, Jr. et al. |
| 3,041,060 A | 6/1962 | Jacobsen |
| 3,122,348 A | 2/1964 | Wilkinson |
| 3,239,184 A | 3/1966 | Kirkeby |
| 3,246,200 A | 4/1966 | Kanter |
| 3,280,322 A | 10/1966 | Kirkeby |
| 3,374,347 A | 3/1968 | Hirose |
| 3,426,190 A | 2/1969 | Bobrick |
| 3,476,931 A | 11/1969 | Fletcher |
| 3,547,390 A | 12/1970 | Mehr |
| 3,584,793 A | 6/1971 | Ilzig et al. |
| 3,713,453 A | 1/1973 | Chiaro et al. |
| 3,820,752 A * | 6/1974 | Oram ............... F16M 11/046 248/284.1 |
| 3,856,251 A | 12/1974 | Miller |
| 3,883,105 A | 5/1975 | Matsumoto |
| 3,973,748 A | 8/1976 | Nagasaka |
| 4,003,536 A | 1/1977 | Sekerich |
| 4,076,351 A | 2/1978 | Wyant |
| 4,080,530 A | 3/1978 | Krogsrud |
| 4,107,769 A | 8/1978 | Saluja |
| 4,160,536 A | 7/1979 | Krogsrud |
| 4,165,530 A | 8/1979 | Sowden |
| 4,166,602 A | 9/1979 | Nilsen et al. |
| 4,208,028 A | 6/1980 | Brown et al. |
| 4,266,747 A | 5/1981 | Souder, Jr. et al. |
| 4,296,906 A | 10/1981 | Matthijsse |
| 4,437,144 A | 3/1984 | Guenther |
| 4,460,148 A | 7/1984 | Sasaki |
| 4,494,177 A | 1/1985 | Matthews |
| 4,517,632 A | 5/1985 | Roos |
| 4,523,732 A | 6/1985 | Biber et al. |
| 4,640,062 A | 2/1987 | Rubik |
| 4,744,019 A | 5/1988 | Krogsrud |
| 4,770,384 A | 9/1988 | Kuwazima et al. |
| 4,815,832 A | 3/1989 | Nagano et al. |
| 4,953,822 A | 9/1990 | Sharber et al. |
| 5,025,359 A | 6/1991 | Saluja et al. |
| 5,078,140 A | 1/1992 | Kwoh |
| 5,151,008 A | 9/1992 | Ishida et al. |
| 5,184,601 A | 2/1993 | Putman |
| 5,186,337 A | 2/1993 | Foster et al. |
| 5,288,043 A | 2/1994 | Tigliev |
| 5,333,103 A | 7/1994 | Cvek |
| 5,340,072 A | 8/1994 | Halbirt |
| 5,348,260 A | 9/1994 | Acevedo |
| 5,417,210 A | 5/1995 | Funda et al. |
| 5,445,166 A | 8/1995 | Taylor |
| 5,572,999 A | 11/1996 | Funda et al. |
| 5,609,316 A | 3/1997 | Tigliev |
| 5,618,090 A | 4/1997 | Montague et al. |
| 5,749,362 A | 5/1998 | Funda et al. |
| 5,755,725 A | 5/1998 | Druais |
| 5,792,135 A | 8/1998 | Madhani et al. |
| 5,800,423 A | 9/1998 | Jensen |
| 5,808,665 A | 9/1998 | Green |
| 5,855,553 A | 1/1999 | Tajima et al. |
| 5,855,583 A | 1/1999 | Wang et al. |
| 6,012,821 A | 1/2000 | Yeaney et al. |
| 6,246,200 B1 | 6/2001 | Blumenkranz et al. |
| 6,331,181 B1 | 12/2001 | Tierney et al. |
| 6,364,888 B1 | 4/2002 | Niemeyer et al. |
| 6,424,885 B1 | 7/2002 | Niemeyer et al. |
| 6,441,577 B2 | 8/2002 | Blumenkranz et al. |
| 6,471,363 B1 | 10/2002 | Howell et al. |
| 6,522,906 B1 | 2/2003 | Salisbury, Jr. et al. |
| 6,594,552 B1 | 7/2003 | Nowlin et al. |
| 6,659,939 B2 | 12/2003 | Moll et al. |
| 6,676,669 B2 | 1/2004 | Charles et al. |
| 6,684,129 B2 | 1/2004 | Salisbury et al. |
| 6,702,805 B1 | 3/2004 | Stuart |
| 6,758,843 B2 | 7/2004 | Jensen |
| 6,786,896 B1 | 9/2004 | Madhani et al. |
| 6,788,018 B1 | 9/2004 | Blumenkranz |
| 6,821,259 B2 | 11/2004 | Rahman et al. |
| 6,933,695 B2 | 8/2005 | Blumenkranz |
| 7,065,811 B2 | 6/2006 | Newkirk et al. |
| 7,254,850 B2 | 8/2007 | Newkirk et al. |
| 7,412,776 B2 | 8/2008 | Iikubo et al. |
| 7,453,227 B2 | 11/2008 | Prisco et al. |
| 7,594,912 B2 | 9/2009 | Cooper et al. |
| 7,763,015 B2 | 7/2010 | Cooper et al. |
| 7,837,674 B2 | 11/2010 | Cooper |
| 7,921,489 B2 | 4/2011 | Newkirk et al. |
| 7,963,913 B2 | 6/2011 | Devengenzo et al. |
| 8,038,108 B2 | 10/2011 | Yasunaga et al. |
| 8,336,138 B2 | 12/2012 | Newkirk et al. |
| 8,348,931 B2 | 1/2013 | Cooper et al. |
| 8,500,722 B2 | 8/2013 | Cooper |
| 8,834,489 B2 | 9/2014 | Cooper et al. |
| 8,899,125 B2 | 12/2014 | Bax et al. |
| 9,023,060 B2 | 5/2015 | Cooper et al. |
| 9,291,793 B2 | 3/2016 | Cooper |
| 9,301,807 B2 | 4/2016 | Duval |
| 9,877,792 B2 | 1/2018 | Cooper |
| 9,968,405 B2 | 5/2018 | Cooper et al. |
| 2001/0030683 A1 | 10/2001 | Howell et al. |
| 2003/0021107 A1 | 1/2003 | Howell et al. |
| 2003/0083673 A1 | 5/2003 | Tierney et al. |
| 2003/0208189 A1 | 11/2003 | Payman |
| 2005/0247412 A1 | 11/2005 | Bengtsson et al. |
| 2006/0176655 A1 | 8/2006 | Hillman et al. |
| 2007/0005045 A1 | 1/2007 | Mintz et al. |
| 2007/0142824 A1 | 6/2007 | Devengenzo et al. |
| 2008/0041536 A1 | 2/2008 | Bengtsson et al. |
| 2008/0147089 A1 | 6/2008 | Loh et al. |
| 2010/0069920 A1 | 3/2010 | Naylor et al. |
| 2011/0023651 A1* | 2/2011 | Cooper ............... A61B 90/50 74/490.02 |
| 2011/0097986 A1 | 4/2011 | Cursetjee et al. |
| 2011/0277775 A1 | 11/2011 | Holop et al. |

(56) References Cited

U.S. PATENT DOCUMENTS

| | | | |
|---|---|---|---|
| 2011/0277776 A1 | 11/2011 | McGrogan et al. | |
| 2011/0282357 A1 | 11/2011 | Rogers et al. | |
| 2011/0282358 A1 | 11/2011 | Gomez et al. | |
| 2012/0059390 A1 | 3/2012 | Mintz et al. | |
| 2012/0227532 A1 | 9/2012 | Huang et al. | |
| 2012/0277764 A1* | 11/2012 | Cooper | A61B 90/10 606/130 |
| 2013/0096576 A1* | 4/2013 | Cooper | A61B 34/30 606/130 |
| 2018/0200008 A1 | 7/2018 | Cooper | |

FOREIGN PATENT DOCUMENTS

| | | | |
|---|---|---|---|
| CN | 1457747 | A | 11/2003 |
| DE | 19742050 | A1 | 3/1999 |
| EP | 24433 | A1 | 3/1981 |
| EP | 0571827 | A1 | 12/1993 |
| EP | 0586464 | B1 | 8/1998 |
| EP | 1568445 | A1 | 8/2005 |
| EP | 1239805 | B1 | 6/2006 |
| EP | 1109497 | B1 | 5/2009 |
| JP | H0630896 | A | 2/1994 |
| JP | H08215211 | A | 8/1996 |
| JP | H08275958 | A | 10/1996 |
| JP | H08280697 | A | 10/1996 |
| JP | H09507131 | A | 7/1997 |
| JP | 2003517883 | A | 6/2003 |
| JP | 2003299674 | A | 10/2003 |
| WO | WO-9009141 | A2 | 8/1990 |
| WO | WO-9507055 | A1 | 3/1995 |
| WO | WO-200399152 | A1 | 12/2003 |
| WO | WO-2004006794 | A1 | 1/2004 |
| WO | WO-2004035270 | A1 | 4/2004 |
| WO | WO-2006079108 | A1 | 7/2006 |

OTHER PUBLICATIONS

Extended European Search Report for Application No. 12185109.1, dated Nov. 17, 2016, 7 pages.

Extended European Search Report for Application No. EP10182817, dated Nov. 19, 2012, 6 pages.

Extended European Search Report for Application No. 11160060.7, dated Jun. 3, 2016, 8 pages.

Herder, Justus L.; Energy-Free Systems: Theory, conception and design of statically balanced spring mechanisms, PhD Dissertation, Delft University of Technology, Delft, The Netherlands, November 200, Internet:< http://mms.tudelft.nl/staff/herder/statbal.htm> Downloaded May 21, 2008.

International Preliminary Report on Patentability for PCT Application No. PCT/US08/51206, dated Jul. 28, 2009, 10 pages.

Learn about Extension Springs, Lee Spring Company, 2015.

PCT/US06/02628 International Search Report dated Jun. 13, 2006, 3 pages.

PCT/US06/02628 Written Opinion of the International Search Authority, dated Jun. 13, 2006, 6 pages.

PCT/US08/051206, Invitation to Pay Additional Fees including a Partial International Search Report dated Jun. 26, 2008, 4 pages.

PCT/US08/51206 International Search Report and Written Opinion of the International Searching Authority, dated Sep. 16, 2008, 17 pages.

Rahman, Tarique; "A Simple Technique to Passively Gravity Balance Articulated Mechanisms," 1995, ASME Transactions on Mechanisms Design.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

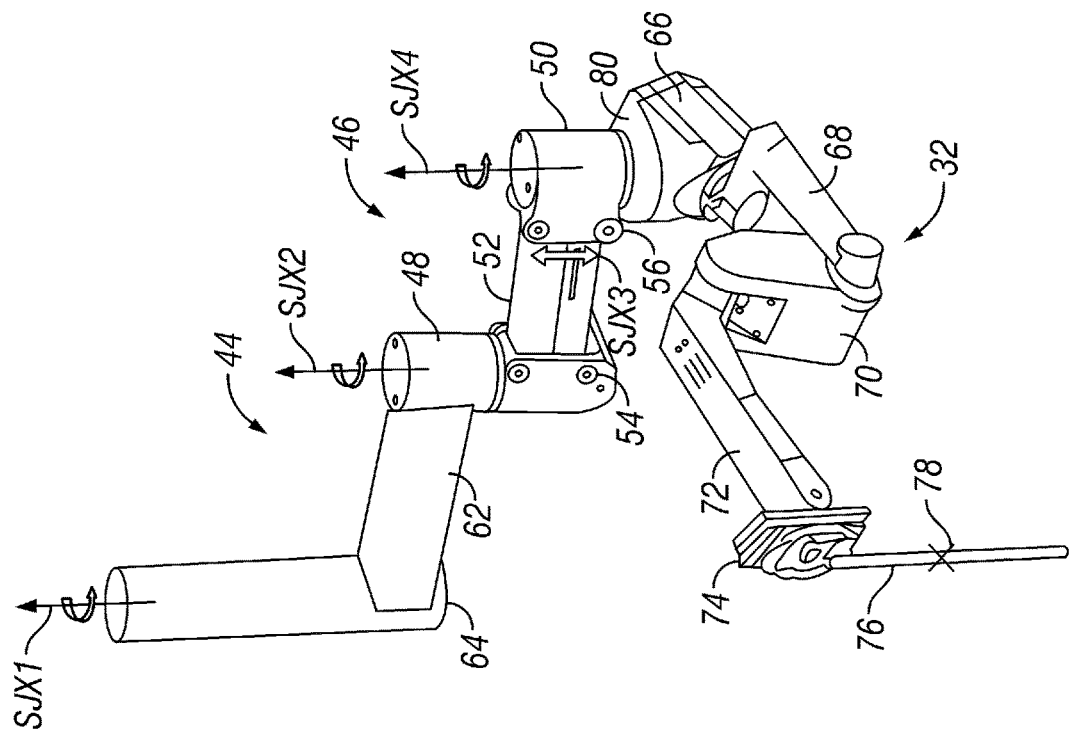
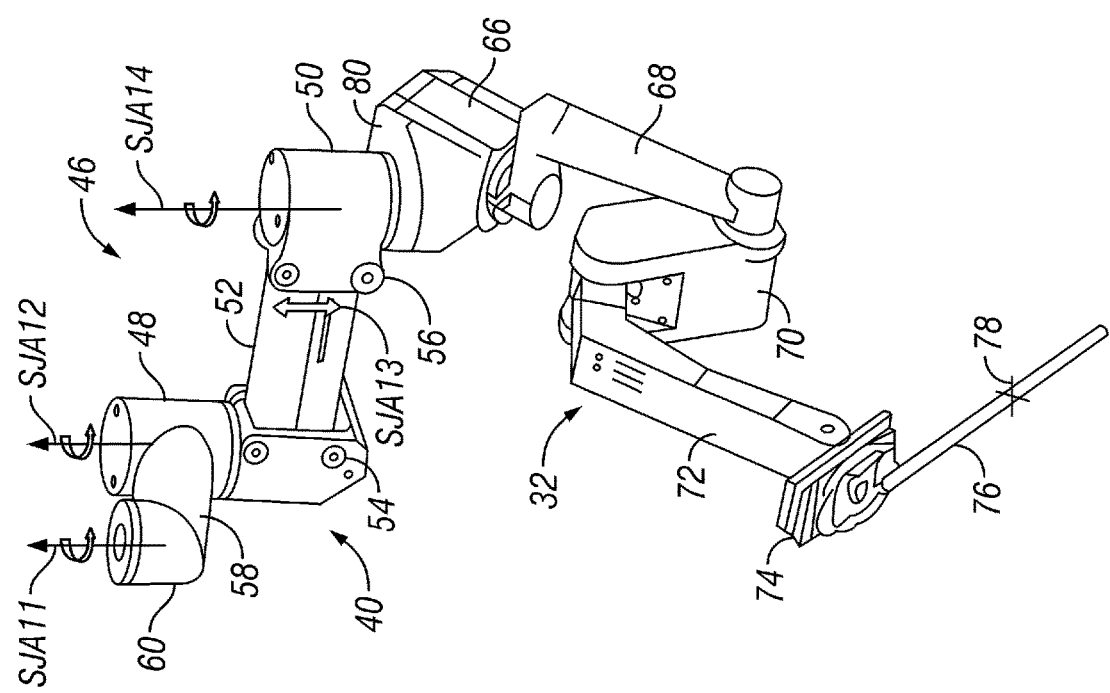

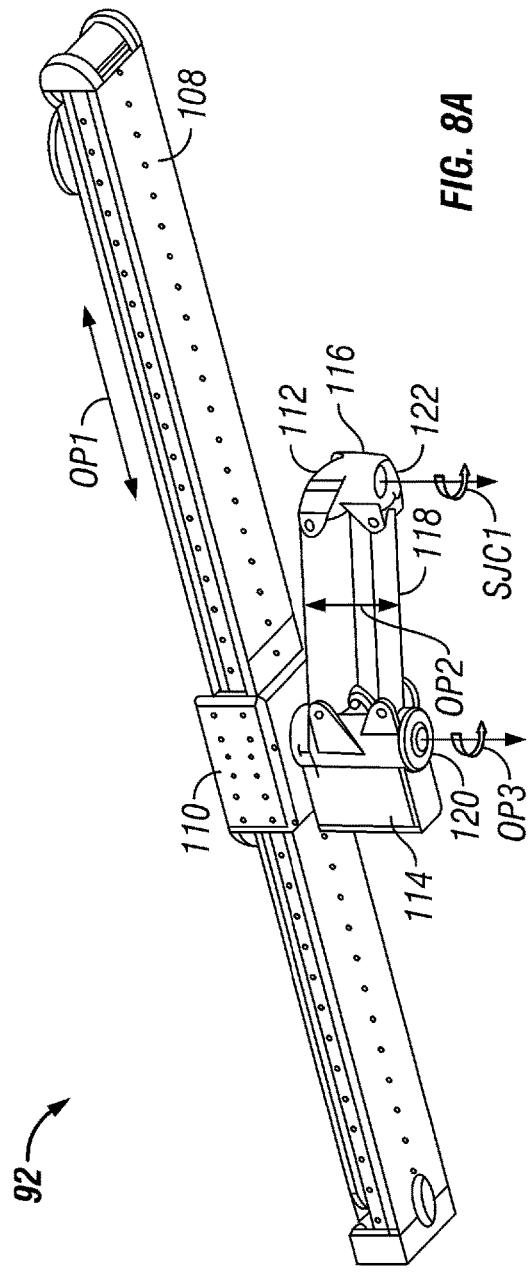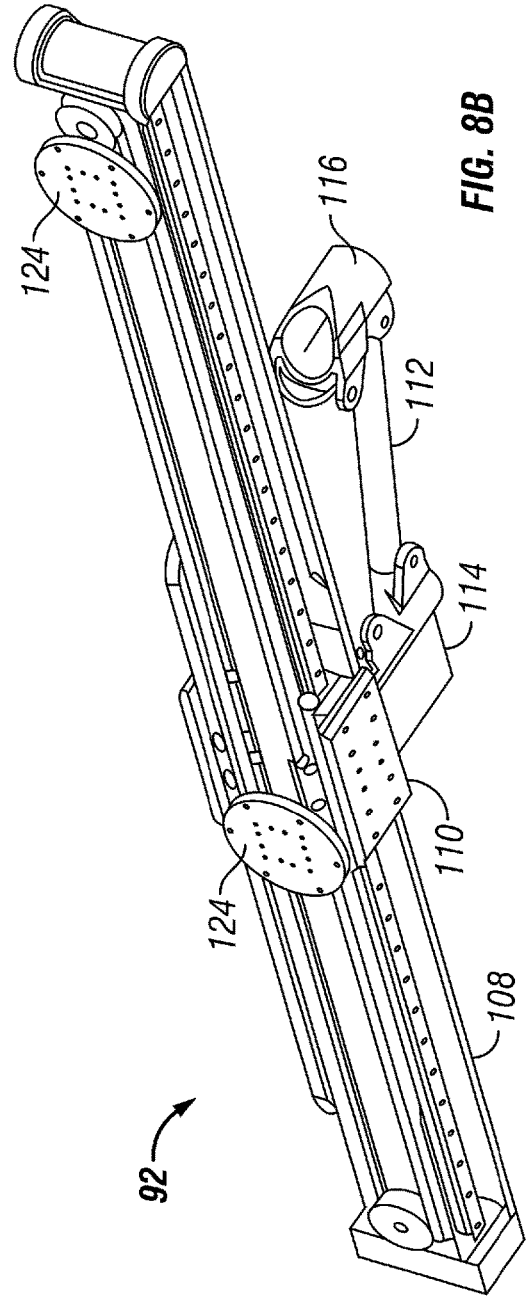

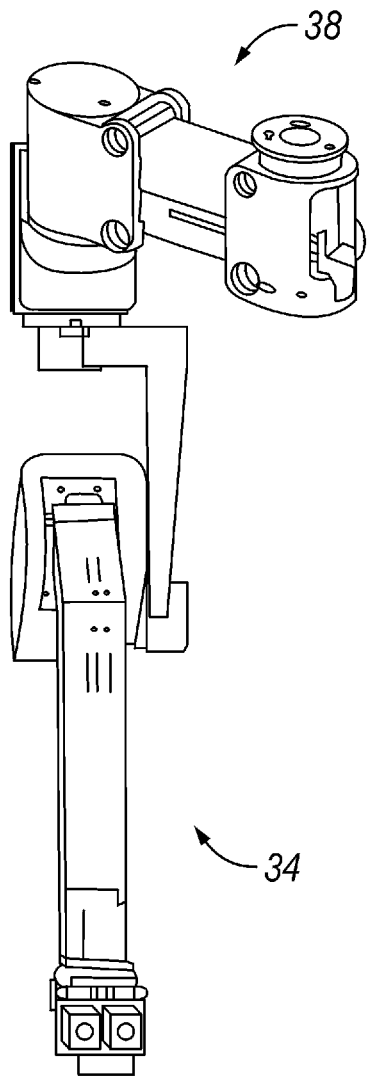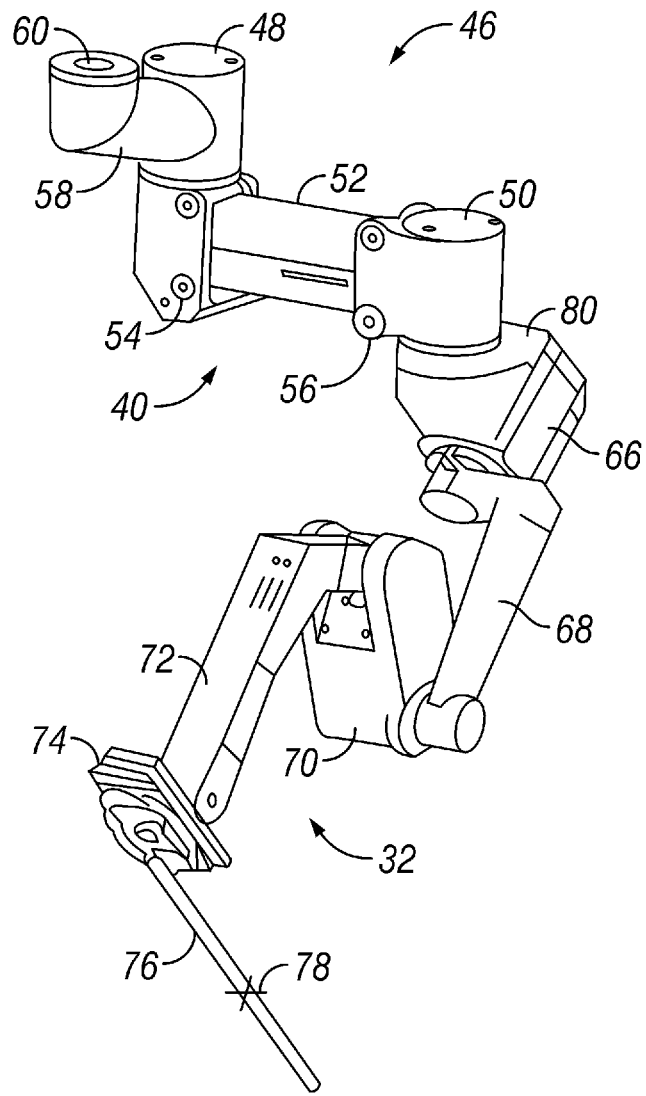
FIG. 9G
FIG. 10A

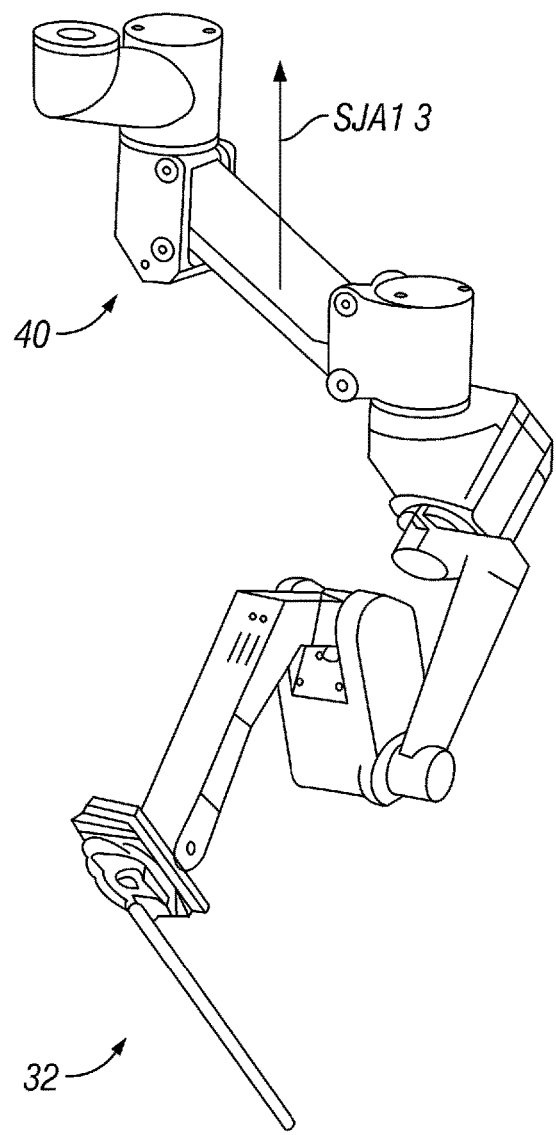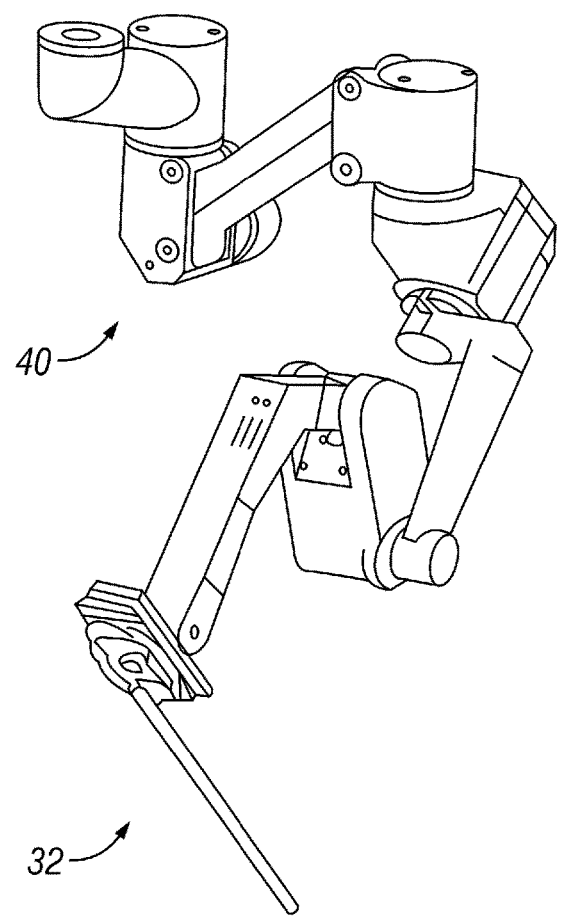
*FIG. 10E*  *FIG. 10F*

MODULAR MANIPULATOR SUPPORT FOR ROBOTIC SURGERY

CROSS-REFERENCE TO RELATED APPLICATIONS

This application is a continuation of U.S. patent application Ser. No. 14/271,763, filed on May 7, 2014 (now U.S. Pat. No. 9,968,405), which is a divisional of U.S. patent application Ser. No. 13/706,738, filed on Dec. 6, 2012 (now U.S. Pat. No. 9,023,060), which is a divisional of U.S. patent application Ser. No. 12/362,299, filed on Jan. 29, 2009 (now U.S. Pat. No. 8,348,931), which is a continuation of U.S. patent application Ser. No. 11/043,688, filed on Jan. 24, 2005 (now U.S. Pat. No. 7,763,015), the full disclosures of which are incorporated herein by reference.

BACKGROUND OF THE INVENTION

The present invention is generally related to medical, surgical, and/or robotic devices and systems. In an exemplary embodiment, the invention provides minimally invasive robotic surgery systems having improved structures for supporting and aligning robotic manipulators, such as manipulators for moving a surgical instrument, an endoscope or other image capture device, with desired surgical sites in a patient body.

Minimally invasive medical techniques are intended to reduce the amount of extraneous tissue which is damaged during diagnostic or surgical procedures, thereby reducing patient recovery time, discomfort, and deleterious side effects. One effect of minimally invasive surgery, for example, is reduced post-operative hospital recovery times. Because the average hospital stay for a standard open surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive robotic surgical or telesurgical systems have been developed to increase a surgeon's dexterity and avoid some of the limitations on traditional minimally invasive techniques. In telesurgery, the surgeon uses some form of remote control, e.g., a servomechanism or the like, to manipulate surgical instrument movements, rather than directly holding and moving the instruments by hand. In telesurgery systems, the surgeon can be provided with an image of the surgical site at the surgical workstation. While viewing a two or three dimensional image of the surgical site on a display, the surgeon performs the surgical procedures on the patient by manipulating master control devices, which in turn control motion of the servo-mechanically operated instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system, such as those described in U.S. Pat. Nos. 6,364,888 and 6,424,885, the full disclosures of which are incorporated herein by reference. The control system typically includes at least one processor which relays input commands from the master controllers to the associated robotic arm and instrument assemblies and back from the instrument and arm assemblies to the associated master controllers in the case of, e.g., force feedback or the like. Mapping of the hand movements to the image displayed from the image capture device can help provide the surgeon with more control over movement of the surgical instruments. One example of a robotic surgical system is the DA VINCI® system available from Intuitive Surgical, Inc. of Sunnyvale, Calif.

The servo-mechanically driven linkage is sometimes referred to as a robotic surgical manipulator. Exemplary linkage arrangements for use as a robotic surgical manipulator during minimally invasive robotic surgery are described in U.S. patent application Ser. No. 10/957,077 and U.S. Pat. Nos. 6,758,843 and 5,800,423, the full disclosures of which are incorporated herein by reference. These linkages make use of a parallelogram arrangement to hold an instrument having a shaft. Such a manipulator structure can mechanically constrain movement of the instrument so that the instrument pivots about a point of spherical rotation positioned in space along the length of the rigid shaft. By aligning this pivot point with the incision point to the internal surgical site (for example, with a trocar or cannula at an abdominal wall during laparoscopic surgery), an end effector of the surgical instrument can be moved without imposing dangerous forces against the abdominal wall. Alternative manipulator structures are described, for example, in U.S. Pat. Nos. 6,702,805; 6,676,669; 5,855,583; 5,808,665; 5,445,166; and 5,184,601, the full disclosures of which are incorporated herein by reference.

A variety of structural arrangements can also be used to support and position the robotic surgical manipulator and the surgical instrument at the surgical site during robotic surgery. Supporting linkage mechanisms, sometimes referred to as set-up joint arms, are often used to position and align each manipulator with the respective incision point in a patient's body. The supporting linkage mechanism facilitates the alignment of a surgical manipulator with a desired surgical incision point. Exemplary supporting linkage mechanism are described in U.S. Pat. Nos. 6,246,200 and 6,788,018, the full disclosures of which are incorporated herein by reference.

While the new telesurgical systems and devices have proven highly effective and advantageous, still further improvements would be desirable. In general, it would be desirable to provide improved minimally invasive robotic surgery systems. It would be particularly beneficial if these improved technologies enhanced the efficiency and ease of use of robotic surgical systems. For example, it would be particularly beneficial to increase maneuverability, improve space utilization in an operating room, provide a faster and easier set-up, inhibit collisions between robotic devices during use, and/or reduce the mechanical complexity and size of these new surgical systems.

BRIEF SUMMARY OF THE INVENTION

The present invention is generally related to medical, surgical, and/or robotic devices and systems. In many embodiments, the present invention provides minimally invasive robotic surgery systems having improved structures for supporting and aligning robotic manipulators, such as manipulators for moving a surgical instrument, an endoscope or other image capture device, with desired surgical incision sites in a patient's body. Improved modular manipulator support can provide several advantages, including increased maneuverability, improved space utilization in an operating room, a faster and easier set-up, collision inhibition between robotic devices during use, and/or reduced mechanical complexity and size of these new surgical systems. Such advantages in turn enhance the efficiency and ease of use of such robotic surgical systems.

In a first aspect of the present invention a robotic surgery system comprises a mounting base, a plurality of surgical instruments, and an articulate support assembly. Each instrument is insertable into a patient through an associated minimally invasive aperture to a desired internal surgical site. The articulate support assembly movably supports the instruments relative to the base. The support generally comprises an orienting platform, a platform linkage movably supporting the orienting platform relative to the base, and a plurality of manipulators mounted to the orienting platform, wherein each manipulator movably supports an associated instrument.

The mounting base preferably comprises a ceiling supported structure so as to permit the articulate support assembly to extend generally downward from the base. A ceiling mounted articulate support assembly advantageously improves space utilization in an operating room, particularly clearing up space adjacent the operating table for personnel and/or other surgical equipment as well as minimizing robotic equipment and cabling on the floor. Further, a ceiling mounted articulate support assembly minimizes the potential for collisions or space conflicts with other adjacent manipulators during a procedure and provides for convenient storage when the robotic surgery system is not in use.

The platform linkage preferably comprises a linear rail, a slidable carriage coupleable to the rail, and at least one arm rotationally coupleable to the carriage on a proximal end and to the orienting platform on a distal end. The platform linkage advantageously enhances maneuverability of the articulate support assembly by accommodating translation of the orienting platform in at least three dimensions as well as rotation of the orienting platform about one axis. The orienting platform's enhanced range of motion permits access to incision sites over a wide range of the patient's body. This may be beneficial when performing complicated and lengthy procedures, such as colon surgery, multi-vessel coronary bypass graft procedures, heart surgery, gastric bypass, and the like, by facilitating quick repositioning of the manipulators mid-operation to alternative surgical sites.

The robotic surgery system further includes a plurality of configurable set-up joint arms coupleable to the orienting platform. Each arm is movably supporting an associated manipulator and defines releasably fixable links and joints that are pre-configurable. In many embodiments, three or more manipulators will be mounted to the orienting platform, often being four or more manipulators, each manipulator being associated with a separate incision site. Each of the four or more incision sites is about 7-15 mm in diameter, and may be considered to be a point, which is typically located at a midpoint of an abdominal wall in the abdomen or next to a rib in the thorax. Preferably, the orienting platform comprises four hubs rotationally coupleable to the plurality of arms and a fifth hub coupleable to the platform linkage, wherein the fifth hub is aligned with a pivot point, which is preferably coincident with the incision site for the endoscope. The fifth hub provides for rotation of the orienting platform about this endoscope manipulator pivot point to allow the plurality of set-up arms to point in the direction in which a surgical procedure is to take place.

Generally, the orienting platform supports three set-up joint arms for movably supporting instrument manipulators and one set-up joint arm for movably supporting an image capture device manipulator. Utilization of the orienting platform to support the individually positionable set-up arms and associated manipulators advantageously results in a relatively small and compact manipulator support structure that is mechanically less complex. For example, the single orienting platform can allow for a faster and easier set-up by avoiding delays and complexities associated with independently configuring each set-up arm.

Each set-up joint arm is simplified in that it has no more than four degrees of freedom. Typically, each arm accommodates translation of the fixable links and joints in one dimension and rotation of the fixable links and joints about two or three axes. At least one set-up joint arm includes at least one balanced, fixable, jointed parallelogram linkage structure extending between a pair of adjacent fixable rotational joints. The jointed parallelogram structure accommodates motion in a generally vertical direction, and the adjacent rotational joints accommodate pivotal motion about vertical axes.

The system may further include a brake system coupled to the articulate support assembly. The brake system releasably inhibits articulation of the fixable links and joints previously configured in at least substantially fixed configuration. The brake system is biased toward the fixed configuration and includes a brake release actuator for releasing the fixable links and joints to a repositionable configuration in which the fixable links and joints can be articulated. The system may further include a joint sensor system coupling a plurality of the fixable links and joints to a servomechanism. The sensor system generates joint configuration signals. The servomechanism includes a computer and the joint sensor system transmits the joint configuration signals to the computer. The computer calculates a coordinate system transformation between a reference coordinate system affixed relative to the mounting base and the instruments using the joint configuration signals.

At least one manipulator is mechanically constrained so that a manipulator base is at a fixed angle relative to horizontal. The at least one manipulator supported by the set-up joint arm is angularly offset relative to horizontal in a range from 40 degrees to about 60 degrees, preferably from about 45 degrees to about 50 degrees. The at least one manipulator supported by the set-up joint auxiliary arm is angularly offset relative to horizontal in a range from 0 degrees to about 20 degrees, preferably by about 15 degrees. The at least one manipulator supported by the set-up joint center arm is angularly offset relative to horizontal in a range from 40 degrees to about 90 degrees, preferably from about 65 degrees to about 75 degrees.

Preferably, at least one manipulator comprises an offset remote center linkage for constraining spherical pivoting of the instrument about a pivot point in space, wherein actuation of the fixable links and joints of the set-up joint arm moves the pivot point. Surprisingly, the set-up arms may be simplified (e.g., with no more than four degrees of freedom) due to the increased range of motion provided by the offset remote center manipulators. This allows for a simpler system platform with less pre-configuration of the set-up joint arms. As such, operating room personnel may rapidly arrange and prepare the robotic system for surgery with little or no specialized training. Exemplary offset remote center manipulators providing for reduced mechanical complexity of the set-up arms are described in further detail in U.S. patent application Ser. No. 10/957,077.

In one embodiment, the offset remote center manipulator generally comprises an articulate linkage assembly having a manipulator base, parallelogram linkage base, a plurality of driven links and joints, and an instrument holder. The manipulator base is rotationally coupled to the parallelogram linkage base for rotation about a first axis. The parallelogram linkage base is coupled to the instrument holder by the plurality of driven links and joints. The driven links and joints define a parallelogram so as to constrain an elongate shaft of the instrument relative to a pivot point when the instrument is mounted to the instrument holder and the shaft is moved in at least one degree of freedom. The first axis and a first side of the parallelogram adjacent the parallelogram linkage base intersect the shaft at the pivot point, and the first side of the parallelogram is angularly offset from the first axis.

In another aspect of the present invention, a modular manipulator support for use in a robotic surgery system is provided. The system comprises a mounting base, a plurality of surgical instruments, and a plurality of manipulators defining driven links and joints for moving an associated instrument so as to manipulate tissues. The support for movably supporting and positioning the manipulator relative to the base includes an orienting platform coupleable to the mounting base and a plurality of arms coupleable to the orienting platform. Each arm movably supports an associated manipulator and defines releasably fixable links and joints that are pre-configurable. The support may further include a display, such as in interactive monitor, coupleable to the orienting platform. This display may be used for set-up purposes, instrument changes, and/or for personnel viewing of a procedure.

In yet another aspect of the present invention, a robotic surgery system comprises a ceiling-height mounting base, a plurality of surgical instruments, and an articulate support assembly movably supporting the instruments relative to the base. The assembly comprising an orienting platform and a plurality of arms associated with a plurality of manipulators. The orienting platform is coupleable to the base so as to permit the articulate support assembly to extend generally downward from the base. The plurality of arms are coupleable to the orienting platform, wherein each arm defines releasably fixable links and joints that are pre-configurable. The plurality of manipulators are coupleable to the arms, each manipulator defining driven links and joints for moving the instruments so as to manipulate tissues.

In still another aspect of the present invention, methods for preparing a robotic surgery system having a mounting base, a plurality of surgical instruments, and an articulate support assembly movably supporting the instruments relative to the base are provided. One method comprising moving an orienting platform to pre-position a plurality of manipulators mounted to the orienting platform by articulating a platform linkage movably supporting the orienting platform relative to the base so that the surgical instruments supported by the manipulators are orientated towards associated minimally invasive apertures. Movement of the orienting platform may comprise translating the orienting platform in three dimensions and/or rotating the orienting platform about one axis. The plurality of manipulators may be moved by articulating a plurality of arms coupleable to the orienting platform. The platform linkage, orienting platform, and/or the arms may be restrained with brake systems so as to prevent further articulation.

A further understanding of the nature and advantages of the present invention will become apparent by reference to the remaining portions of the specification and drawings.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

FIGS. 6A and 6B are perspective views of the set-up joint arm and the set-up joint auxiliary arm, respectively, of the manipulator support of FIG. 5A.

FIGS. 8A and 8B are perspective views from below and above of a platform linkage for movably supporting the manipulator support of FIG. 5A.

FIGS. 9A through 9G illustrate perspective and top views of the set-up joint center arm supporting and positioning an endoscope camera robotic manipulator.

FIGS. 10A through 10H illustrate perspective and top views of the set-up joint arm supporting and positioning a patient side robotic manipulator.

DETAILED DESCRIPTION OF THE INVENTION

Figure 1:
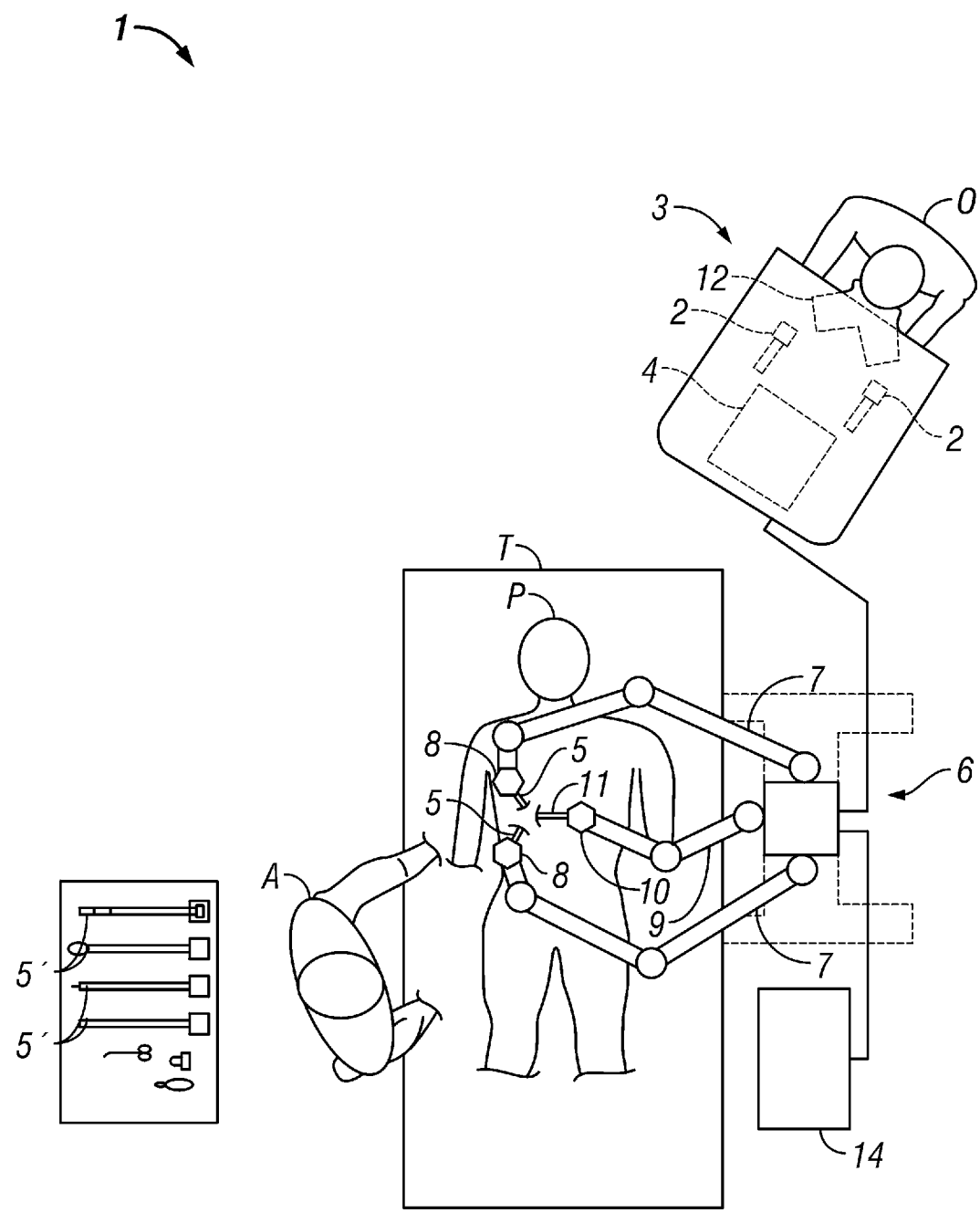
FIG. 1 is a schematic plane view of a portion of an operating theater illustrating a robotic surgical system, including a master surgeon console or workstation for inputting a surgical procedure and a robotic patient side cart for robotically moving surgical instruments having surgical end effectors at surgical sites.

FIGS. 1 through 4 illustrate a robotic surgical system 1 for performing minimally invasive robotic surgery, which is described in more detail in U.S. Pat. No. 6,246,200. An operator O (generally a surgeon) performs a minimally invasive surgical procedure on patient P lying on operating table T, the operator O manipulating one or more input devices or masters 2 at a surgeon's console 3. In response to the surgeon's inputs, a computer processor 4 of console 3 directs movement of endoscopic surgical instruments or tools 5, effecting servo-mechanical movement of the instruments via a robotic patient side system 6 (a cart-mounted system in this example).

Typically, patient side system or cart 6 includes at least three robotic manipulator arms. Two set-up joint arms or linkages 7 (mounted at the sides of cart 6 in this example) support and position servo-manipulators 8 which drive surgical tools 5; and one set-up joint arm or linkage 9 (mounted at the center of cart 6 in this example) supports and positions servo-manipulator 10 which controls the motion of an endoscope camera probe 11, which captures an image (preferably stereoscopic) of the internal surgical site.

The image of the internal surgical site is shown to surgeon or operator O by a stereoscopic display viewer 12 in surgeon's console 3, and is simultaneously shown to assistant A by an assistant's display 14. Assistant A assists in pre-positioning the manipulator 8 and 10 relative to patient P using set-up linkage arms 7, 9, in swapping tools 5 in one or more of surgical manipulator 8 (and/or 10) for alternative surgical tools or instruments 5', in operating related non-robotic medical instruments and equipment, and the like.

In general terms, the arms or linkages 7, 9 comprise a positioning linkage or set-up arm portion of patient side system 6, typically remaining in a fixed configuration while tissue is manipulated, and the manipulators 8, 10 comprise a driven portion which is actively articulated under the direction of surgeon's console 3. The manipulators 8, 10 are primarily used for master/slave tissue manipulation, while the set-up arms 7, 9 are used for positioning and/or configuring the manipulators 8, 10 before use, when repositioning the patient, operating table, incision points, and the like.

For convenience in terminology, a manipulator such as 8 actuating tissue affecting surgical tools is sometimes referred to as a PSM (patient side manipulator), and a manipulator such as 10 controlling an image capture or data acquisition device, such as endoscope 11, is sometimes referred to as an ECM (endoscope-camera manipulator), it being noted that such telesurgical robotic manipulators may optionally actuate, maneuver and control a wide variety of instruments, tools and devices useful in surgery.

Figure 2:
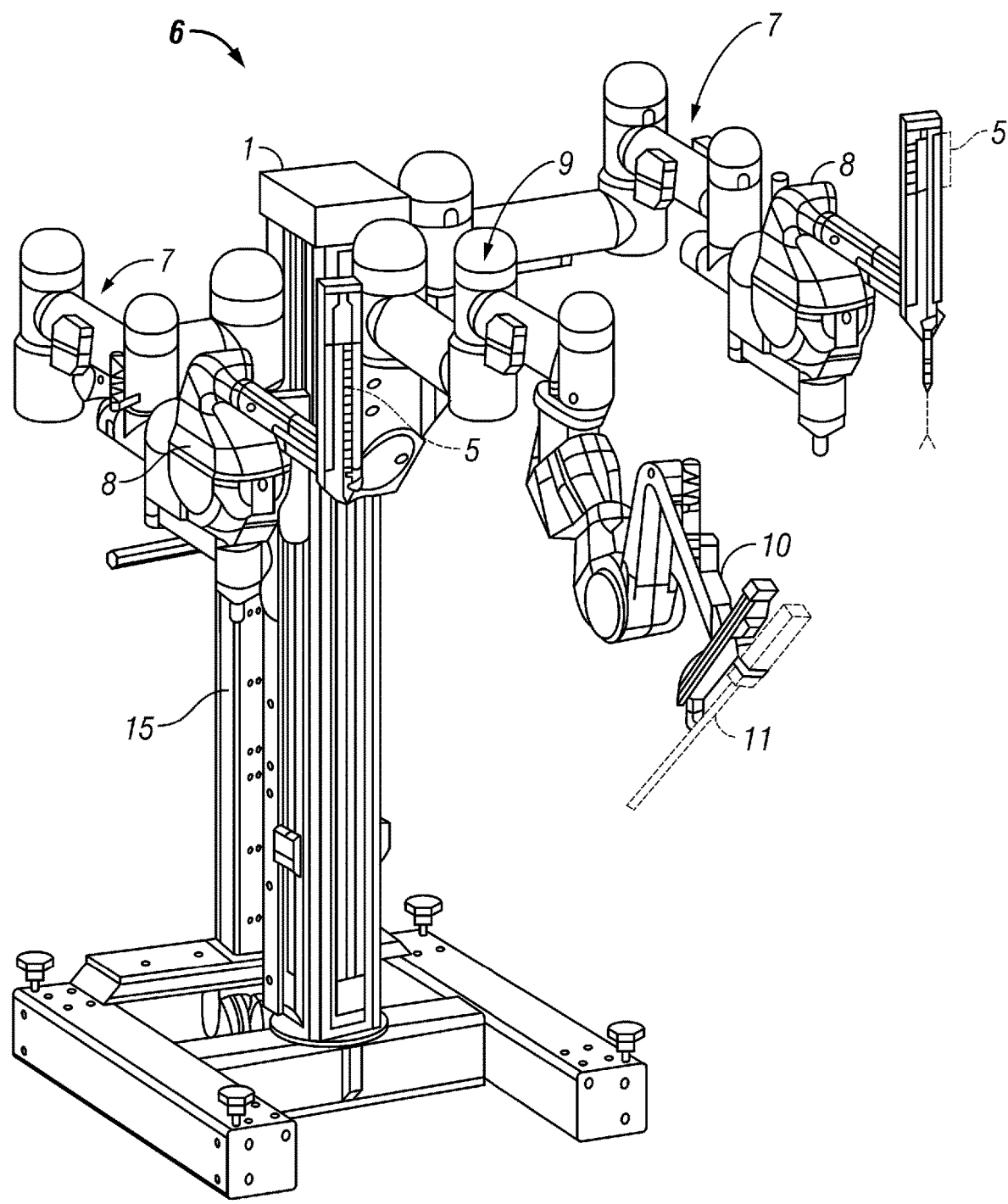
FIG. 2 is a perspective view of the robotic patient side cart or stand, including positioning linkages which allow two patient side robotic manipulators and one endoscope camera robotic manipulator to be pre-configured.

FIG. 2 illustrates a perspective view of the cart mounted telesurgical patient side system 6 of FIG. 1, including two PSM's 8 and one ECM 10. Cart system 6 includes a column 15 which in turn mounts three positioning linkages or set-up arms, including two PSM set-up arms 7, each supporting one of the PSM's 8, and one ECM set-up arm 9 supporting ECM 10. The PSM set-up arms 7 each have six degrees of freedom, and are mounted one on each side of centrally mounted ECM set-up arm 9. The ECM set-up arm 9 shown has less than six degrees of freedom, and ECM 10 may not include all of the tool actuation drive system provided for articulated surgical instruments, such as are typically included in PSM 8. Each PSM 8 releasably mounts surgical tool 5 (shown in dashed lines) and ECM 10 releasably mounts endoscope probe 11 (shown in dashed lines).

Figure 3B:
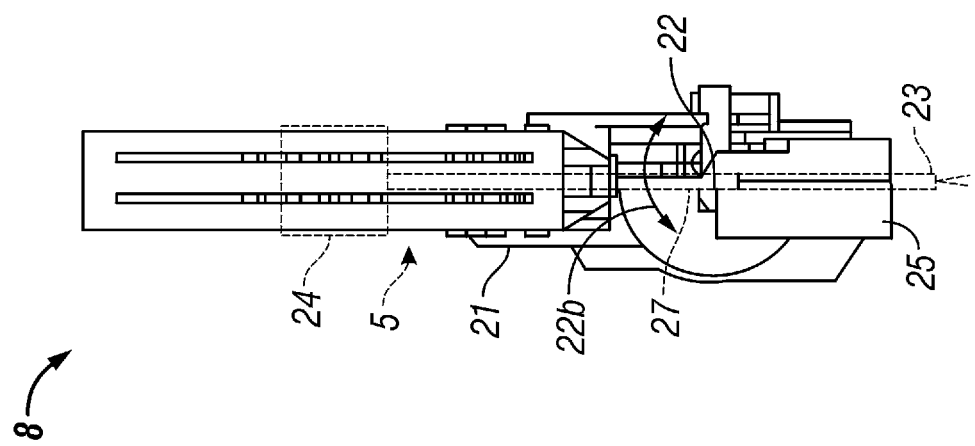
FIGS. 3A and 3B are side and front views, respectively, of the linkage of the robotic manipulators of FIG. 2.
Figure 3A:
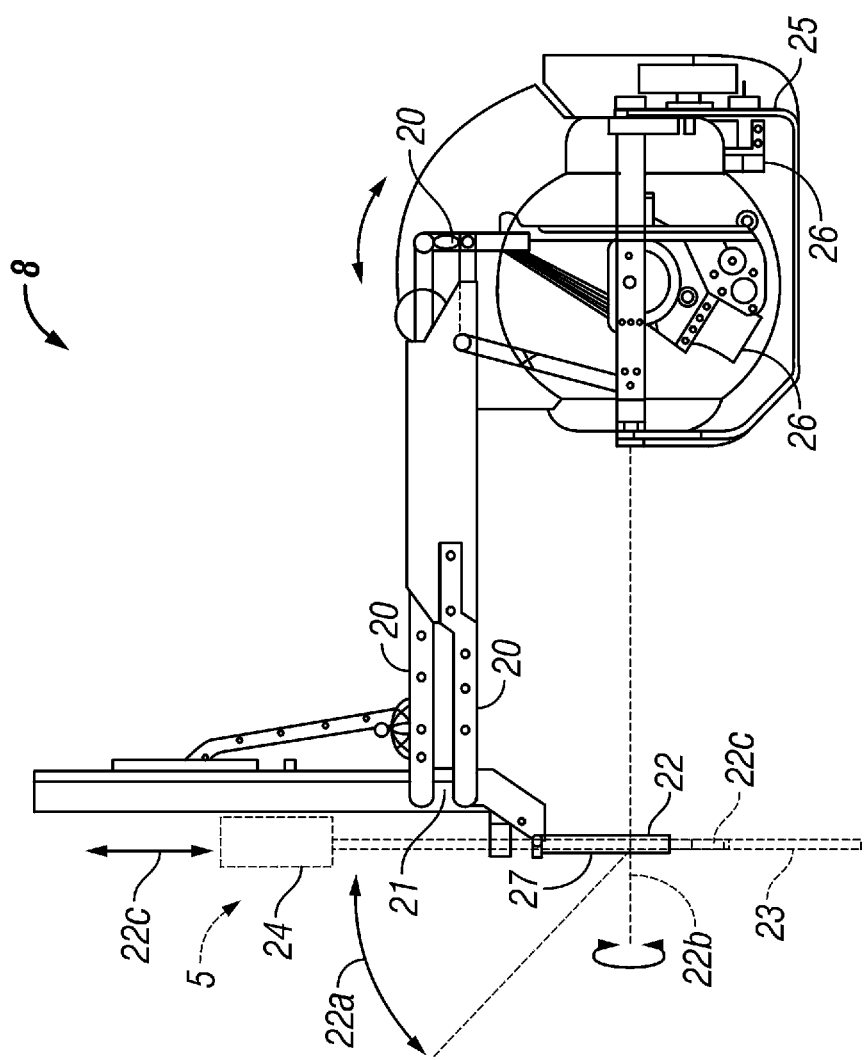

FIGS. 3A and 3B are side and front views, respectively, of the linkage of the robotic surgical manipulator or PSM 8 of FIG. 2, having a remote center mechanism. PSM 8 is one prior art example of a manipulator which may be mounted and supported by a cart mount 6, ceiling mount, or floor/pedestal mount. In this example, the PSM 8 preferably includes a linkage arrangement 20 that constrains movement of tool interface housing 21 and mounted instrument or tool 5. More specifically, linkage 20 includes rigid links coupled together by rotational joints in a parallelogram arrangement so that housing 21 and tool 5 rotate around a point in space 22, as more fully described in issued U.S. Pat. No. 6,758,843.

The parallelogram arrangement of linkage 20 constrains rotation to pivoting, as indicated by arrow 22a in FIG. 3A, about an axis, sometimes called the pitch axis, which is perpendicular to the page in that illustration and which passes through pivot point 22. The links supporting the parallelogram linkage are pivotally mounted to set-up joint arms (7 in FIG. 2) so that tool 5 further rotates about an axis 22b (FIG. 3B), sometimes called the yaw axis. The pitch and yaw axes intersect at the remote center 22, which is aligned along a shaft 23 of tool 5. Tool 5 has still further driven degrees of freedom as supported by manipulator 8, including sliding motion of the tool along insertion axis 22c. Tool 5 includes proximal housing 24 which mounts to manipulator interface housing 21. Interface housing 21 both provides for motion of the tool 5 along axis 22c and serves to transfer actuator inputs to tool 5 from the end effector actuator servo-mechanisms of PSM 8. In this example of a remote center system, the parallelogram arrangement 20 is coupled to tool 5 so as to mechanically constrain the tool shaft 23 to rotation about pivot point 22 as the servomechanism actuates tool motion according to the surgeon's control inputs.

As tool 5 slides along axis 22c relative to manipulator 8, remote center 22 remains fixed relative to mounting base 25 (mounting point to set-up arm 7) of manipulator 8. Hence, the entire manipulator 8 is generally moved to re-position remote center 22. Linkage 20 of manipulator 8 is driven by a series of motors 26 (FIG. 3A). These motors actively move linkage 20 in response to commands from a processor (4 in FIG. 1). Motors 26 are further coupled to tool 5 so as to rotate the tool about axis 22c, and may articulate a wrist (29 in FIG. 4) at the distal end of the tool 5 about at least one, and often two, degrees of freedom. Additionally, motors 26 can be used to actuate an articulatable end effector of the tool for grasping tissues in the jaws of a forceps or the like. Motors 26 may be coupled to at least some of the joints of tool 5 using cables, as more fully described in U.S. Pat. No. 5,792,135, the full disclosure of which is also incorporated herein by reference. As described in that reference, the manipulator 8 will often include flexible members for transferring motion from the drive components to the surgical tool 5. For endoscopic procedures, manipulator 8 will often include a cannula 27. Cannula 27, which may be releasably coupled to manipulator 8, supports tool 5, preferably allowing the tool to rotate and move axially through the central bore of the cannula 27.

Figure 4:
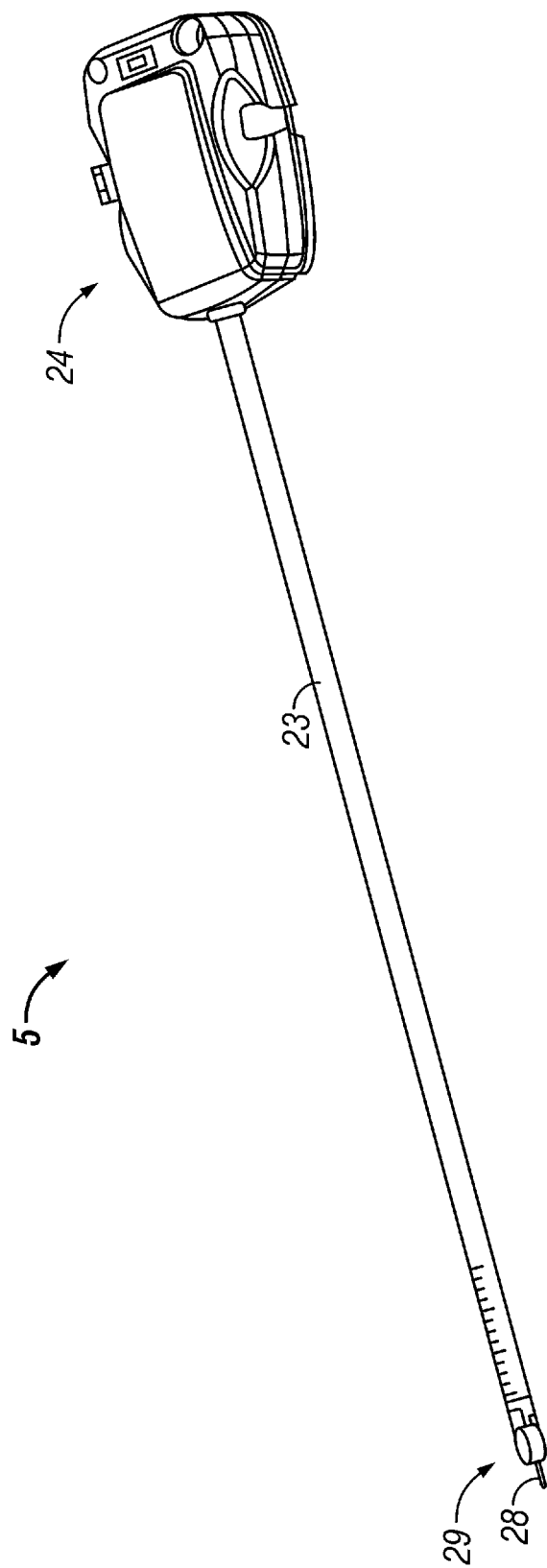
FIG. 4 is a perspective view of an articulated surgical instrument for use in the system of FIG. 1.

FIG. 4 illustrates an exploded perspective view of the articulated surgical tool or instrument 5 and proximal housing 24, that may be employed in the system of FIG. 1. Tool 5 includes elongate shaft 23 supporting end effector 28 relative to proximal housing 24. Proximal housing 24 is adapted for releasably mounting and interfacing instrument 5 to a manipulator (e.g., PSM 8 in FIGS. 1, 2, 3A, and 3B), and for transmitting drive signals and/or motion between the manipulator 8 and end effector 28. An articulated wrist mechanism 29 may provide two degrees of freedom of motion between end effector 28 and shaft 23, and the shaft 23 may be rotatable relative to proximal housing 24 so as to provide the end effector 28 with three substantially orientational degrees of freedom within the patient's body.

Figure 5A:
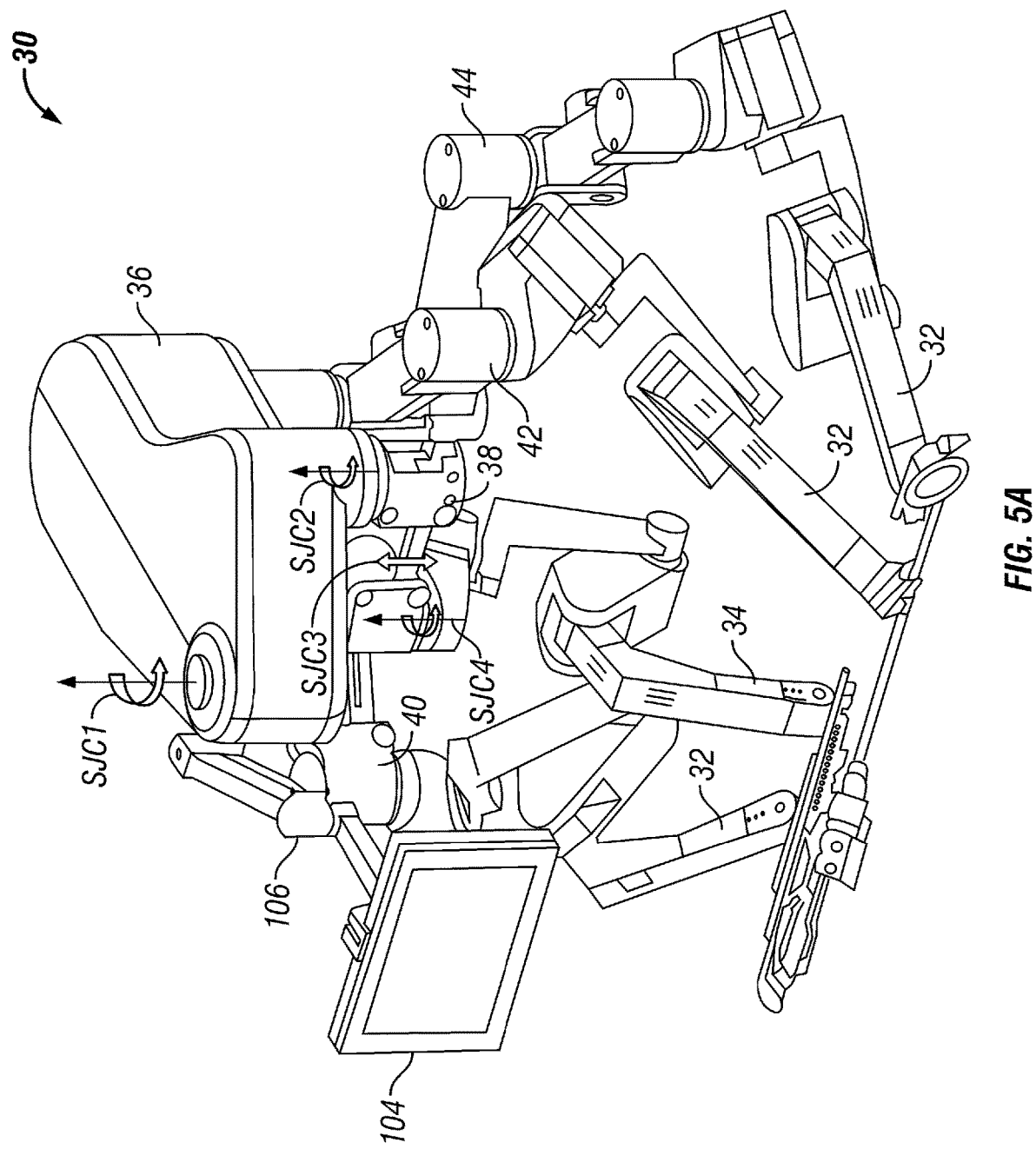
FIGS. 5A and 5B are perspective views from above of an exemplary modular manipulator support constructed in accordance with the principles of the present invention.
Figure 5B:
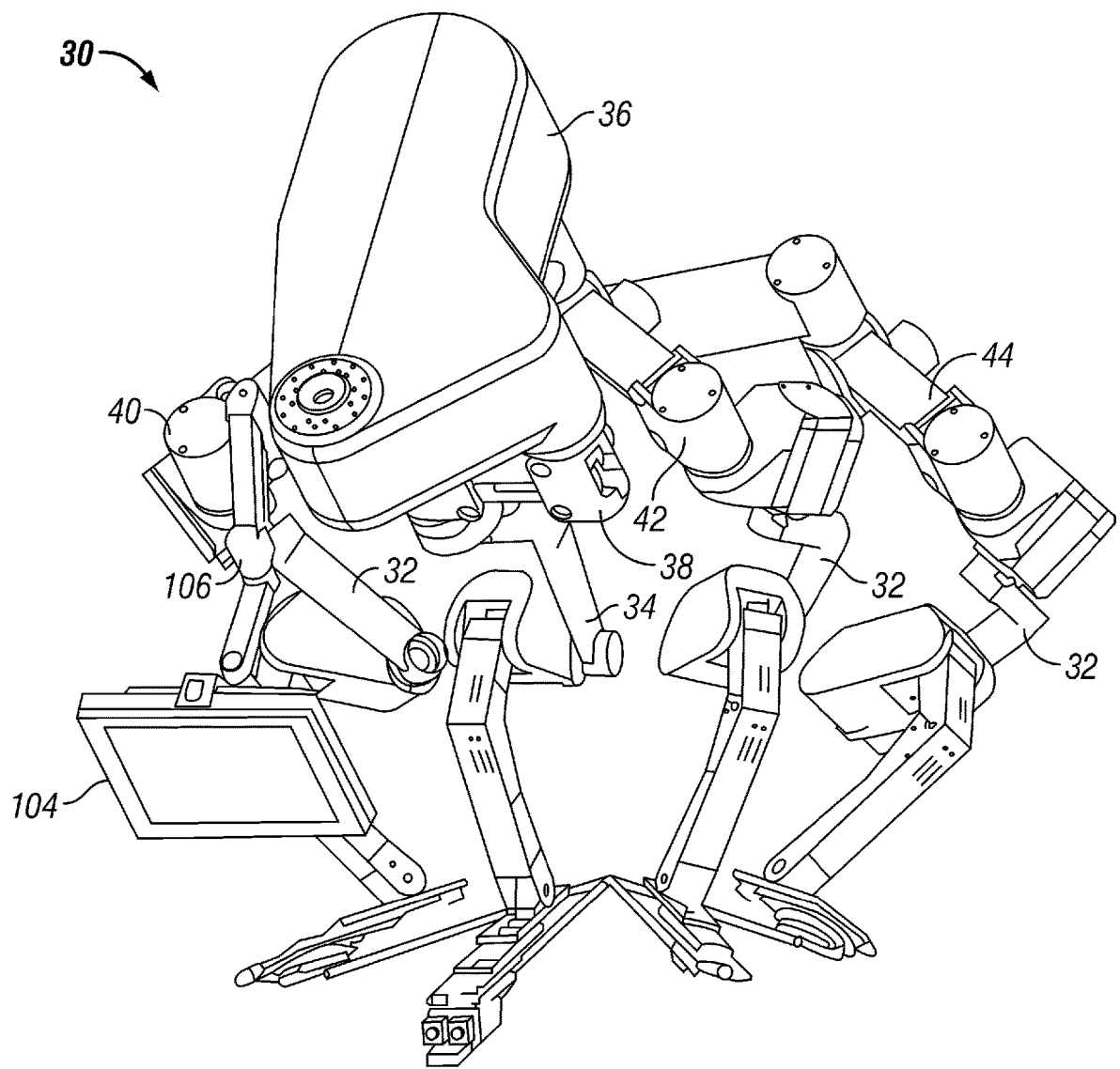

Referring now to FIGS. 5A and 5B, perspective views from above of an exemplary modular manipulator support assembly 30 constructed in accordance with the principles of the present invention are illustrated. The modular manipulator support 30 aligns and supports robotic manipulators, such as patient side manipulators 32 or endoscope camera manipulators 34, with a set of desired surgical incision sites in a patient's body. The modular manipulator support assembly 30 generally includes an orienting platform 36 and a plurality of configurable set-up joint arms 38, 40, 42, 44 coupleable to the orienting platform 36. Each arm 38, 40, 42, 44 is movably supporting an associated manipulator 32, 34 which in turn movably supports an associated instrument. It will be appreciated that the above depictions are for illustrative purposes only and do not necessarily reflect the actual shape, size, or dimensions of the modular manipulator support assembly 30. This applies to all depictions hereinafter.

The orienting platform 36 generally supports two set-up joint arms 40, 42 (SJA1 right and SJA2 left) and one optional auxiliary arm 44 (SJX) for movably supporting the associated patient side manipulators 32. Typically, each arm accommodates translation of the patient side manipulator in three dimensions (x, y, z) and rotation of the patient side manipulator about one vertical axis (azimuth). Further perspective views of the set-up joint right arm 40 and the set-up joint auxiliary arm 44 are shown respectively in FIGS. 6A and 6B. Generally, the right and left arms 40, 42 support manipulators which correspond to the right and left surgeon controls while the auxiliary or assistant arm 44 provides for additional variation in manipulator positioning which is of particular benefit during complex surgeries, such as cardiac surgery. The orienting platform 36 further supports one set-up joint center arm 38 (SJC) for movably supporting the endoscope camera manipulator 34. It will be appreciated that the set-up arms 38, 40, 42, 44 may interchangeably support and position instrument 32 or camera 34 manipulators. Utilization of the orienting platform 36 to support the individually positionable set-up arms 38, 40, 42, 44 and associated manipulators 32, 34 advantageously results in a simplified single support unit having a relatively scaled down, compact size. For example, the single orienting platform 36 may obviate any need to individually arrange and mount each set-up arm 38, 40, 42, 44 to a mounting base, which is often confusing and cumbersome. This in turn allows for a faster and easier set-up.

Figure 9A:
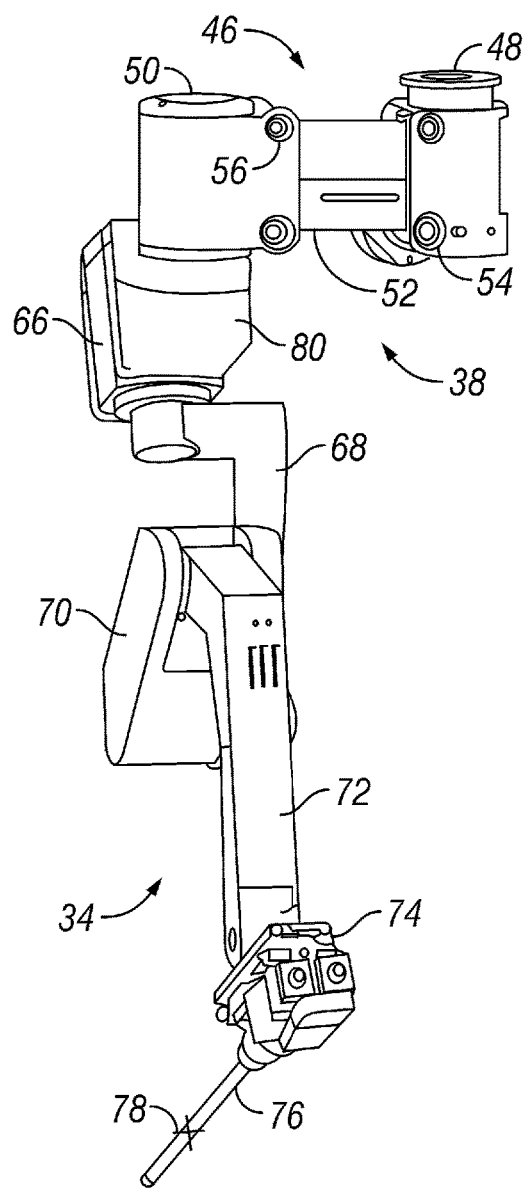

Referring to FIGS. 6A, 6B, 9A, each set-up joint arm 38, 40, 42, 44 defines releasably fixable links and joints that are pre-configurable. In a preferred embodiment, each set-up joint arm 38, 40, 42, 44 includes at least one balanced, fixable, jointed parallelogram linkage structure 46 extending between a pair of adjacent fixable rotational joints 48, 50. The jointed parallelogram structure 46 accommodates motion in a generally vertical direction, and the adjacent rotational joints 48, 50 accommodate pivotal motion about vertical axes as described in more detail below. One or more linear or curved sliding axes could be used in lieu of any or all of the rotary ones. Each of the parallelogram structures 46 may have a generally similar structure, in this example comprising a link 52 of variable length, a proximal bracket 54, and a distal bracket 56. The link 52 is pivotally jointed to proximal and distal brackets 54, 56 respectively in a vertically-oriented planar parallelogram configuration. This permits rotational motion of the link 52 in the vertical plane, while constraining the brackets 54, 56 to remain substantially parallel to one another as the parallelogram 46 deforms by joint rotation 48, 50. As shown in FIG. 6A, an additional link 58 may be rotationally coupled by an additional pivot 60 for set-up joint arms 40, 42. An additional auxiliary link 62 of longer length may be rotationally coupled by an additional auxiliary pivot 64 for set-up joint auxiliary arm 44. As shown in FIG. 9A, the set-up joint center arm 38 will comprise a relatively short, rigid arm defined primarily by the parallelogram structure 46. The set-up joint arms 38, 40, 42, 44 may be balanced by a variety of mechanisms including weights, tension springs, gas springs, torsion springs, compression springs, air or hydraulic cylinders, torque motors, or combinations thereof.

Each set-up joint arm 38, 40, 42, 44 has surprisingly simplified kinematics (e.g., with no more than four degrees of freedom) due to the improved range of motion provided by the manipulators 32, 34. Typically, the arms accommodate translation of the fixable links and joints in a generally vertical direction as denoted by arrow SJC 3 for arm 38 in FIG. 5A, arrow SJA1 3 for arm 40 in FIG. 6A, and arrow SJX 3 for arm 44 in FIG. 6B. The arms also accommodate rotation of the fixable links and joints about two or three vertical axes. As seen in FIG. 6A, arrows SJA1 1, SJA1 2, and SJA1 4 illustrate the rotational joints 60, 48, 50 respectively of the set-up joint arm 40. The translational and rotational axes for the left set-up joint arm 42 (SJA2) is identical to that of the right arm 40 (SJA1) illustrated in FIG. 6A. FIG. 6B denotes the rotational joints 64, 48, 50 of the set-up joint auxiliary arm 44 by arrows SJX 1, SJX 2, and SJX 4 respectively. Arrows SJC 2 and SJC 4 illustrate the rotational joints 48, 50 respectively of the set-up joint center arm 38 in FIG. 5A. The arms 38, 40, 42, 44 may be power operated, computer controlled, manually pre-configured, or a combination thereof. Preferably, joints SJA1 1, SJA2 1, and SJX 1 of the set-up joint arms 40, 42 and the auxiliary arm 44 are motorized while the other joints and set-up joint center arm 38 are manually positioned. Motors may be located within the plurality of fixable links or orienting platform to drive pulley and belt mechanisms.

The fixable joints 48, 50, 62, 64 of the set-up arms 38, 40, 42, 44 typically include a brake system to allow the joints to be locked into place after the arms are appropriately deployed. The brake system releasably inhibits articulation of the fixable links 52, 58, 62 and joints 48, 50, 62, 64 previously configured in at least substantially fixed configuration. The brake system is preferably biased toward the fixed configuration and includes a brake release actuator for releasing the fixable links 52, 58, 62 and joints 48, 50, 62, 64 to a repositionable configuration in which the fixable links and joints can be articulated. The system may further include a joint sensor system coupling a plurality of the fixable links 52, 58, 62 and joints 48, 50, 62, 64 to a servomechanism. The sensor system generates joint configuration signals. The servomechanism includes a computer and the joint sensor system transmits the joint configuration signals to the computer. The computer calculates a coordinate system transformation between a reference coordinate system affixed relative to a mounting base and the instruments using the joint configuration signals.

Referring again to FIGS. 6A, 6B, 9A, the manipulators 32, 34 are mechanically constrained so that a manipulator base 66 is at a fixed angle relative to horizontal. As shown in FIG. 6A, the manipulator 32 supported by the set-up joint arm 40 is angularly offset relative to horizontal in a range from 40 degrees to about 60 degrees, preferably from about 45 degrees to about 50 degrees. As shown in FIG. 6B, the manipulator 32 supported by the set-up joint auxiliary arm 44 is angularly offset relative to horizontal in a range from 0 degrees to about 20 degrees, preferably by about 15 degrees. As shown in FIG. 9A, the manipulator 34 supported by the set-up joint center arm 38 is angularly offset relative to horizontal in a range from 40 degrees to about 90 degrees, preferably from about 65 degrees to about 75 degrees.

Preferably, the manipulators 32, 34 comprise offset remote center linkages for constraining spherical pivoting of the instrument about pivot points in space, wherein actuation of the fixable links 52, 58, 62 and joints 48, 50, 62, 64 of the set-up joint arms 38, 40, 42, 44 moves the pivot points. As discussed above, the overall complexity of the robotic surgical system may be reduced due to the improved range of motion of the system. Specifically, the number of degrees of freedom in the set-up joints arms 38, 40, 42, 44 may be reduced (e.g., less than six degrees of freedom). This allows for a simpler system platform requiring less pre-configuration of the set-up joint arms 38, 40, 42, 44. As such, operating room personnel may rapidly arrange and prepare the robotic system for surgery with little or no specialized training. Exemplary offset remote center manipulators 32, 34 providing for reduced mechanical complexity of the set-up arms 38, 40, 42, 44 are described in further detail in U.S. patent application Ser. No. 10/957,077.

In the embodiment illustrated in FIGS. 6A, 6B, 9A, the offset remote center manipulator 32, 34 generally includes the manipulator base 66, a parallelogram linkage base 68, a plurality of driven links and joints 70, 72, and an instrument holder 74. The manipulator base 66 is rotationally coupled to the parallelogram linkage base 68 for rotation about a first axis, also known as the yaw axis. The parallelogram linkage base 68 is coupled to the instrument holder 74 by rigid links 70, 72 coupled together by rotational pivot joints. The driven links and joints 70, 72 define a parallelogram so as to constrain an elongate shaft of the instrument or cannula 76 relative to a center of rotation (pivot point) 78 when the instrument is mounted to the instrument holder 74 and the shaft is moved along a plane of the parallelogram. The first axis and a first side of the parallelogram adjacent the parallelogram linkage base 68 intersect the shaft at the center of rotation 76, wherein the first side of parallelogram is angularly offset from the first axis.

The manipulator base 66 of the surgical manipulators 32, 34 is mounted and supported at a constant elevation angle by set-up arms 38, 40, 42, 44, as described above in detail. The manipulator base 66 in this embodiment is fixed to a manipulator base support 80 of the set-up arms 38, 40, 42, 44 by screws or bolts. Although the exemplary set-up arms 38, 40, 42, 44 have a manipulator base support 80 suited to the geometry of a remote center manipulator 32, 34, manipulator base support 80 may take on a variety of alternative support configurations to suit other telesurgical manipulators. For example, the manipulator base support may be configured to support further alternative remote center manipulators, natural center manipulators, computed center manipulators, software center manipulators, and manipulators employing a combination of these functional principles. Further, as noted above, the manipulator base support 80 of the set-up arms 38, 40, 42, 44 may interchangeably support and position instrument 32 or camera 34 manipulators.

Referring now to FIGS. 7A through 7D, further perspective views from above and below of the orienting platform 36 are illustrated. The orienting platform 36 comprises a generally horizontal grand piano shaped platform having four hubs 82, 84, 86, 88 rotationally coupleable to the plurality of arms 38, 40, 42, 44 respectively, as shown in the view from below of FIGS. 7B and 7C. In particular, rotational joint 48 of set-up joint center arm 38 supporting the endoscope camera manipulator 34 is rotationally coupled to hub 82 which offset to the side of the orienting platform 36. The rotational joints 60 of the right and left set-up joint arms 40, 42 supporting the patient side manipulators 32 are rotationally coupled to hubs 84, 86 respectively of the orienting platform 36. Lastly, the rotational joint 64 of set-up joint auxiliary arm 44 supporting the patient side manipulator 32 is rotationally coupled to hub 88. Hub 88 is on the midline of the orienting platform 36 so that the auxiliary arm 44 may be utilized on either the left or rights side. In the case of a five set-up joint arm support, a hub may be positioned on each side of the midline similar to the positioning of hubs 84 and 86 with an auxiliary arm for the right side and another auxiliary arm for the left side. The shape of the orienting platform 36 as well as the relative locations of the hubs 82, 84, 86, 88, 90 further contribute to the increased maneuverability of the system as well as collision inhibition between arms and/or manipulators.

Figure 7A:
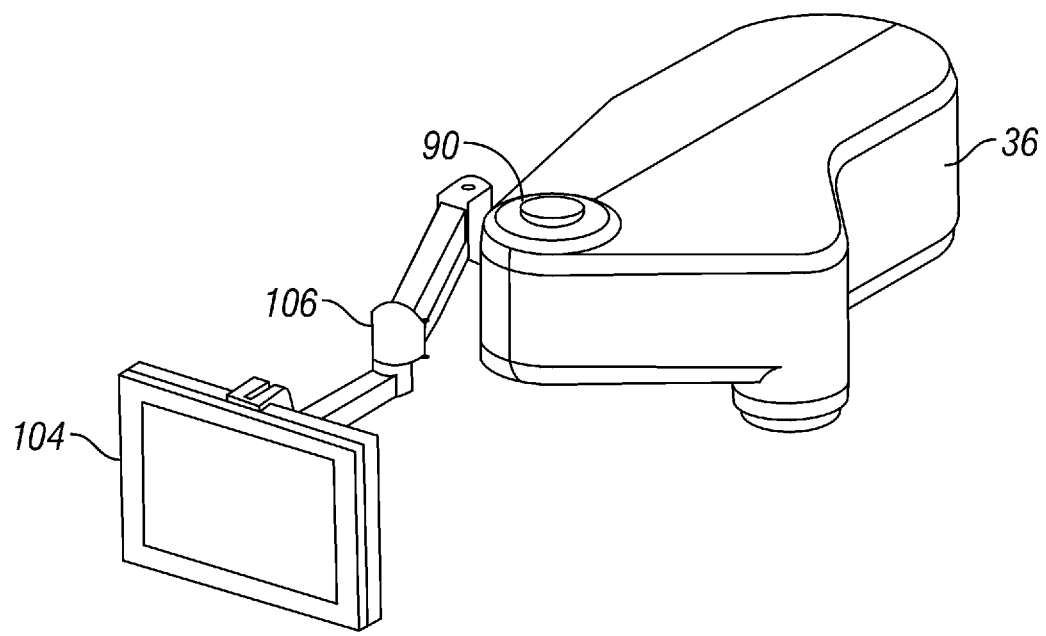
FIGS. 7A through 7D are perspective views from above and below of the orienting platform of the manipulator support of FIG. 5A.
Figure 7B:
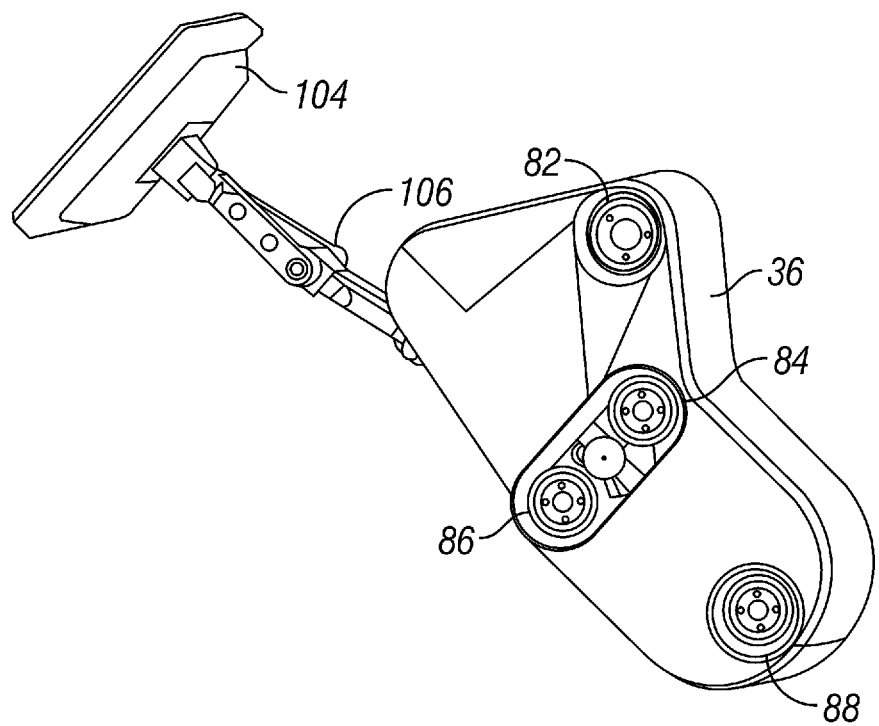
Figure 7C:
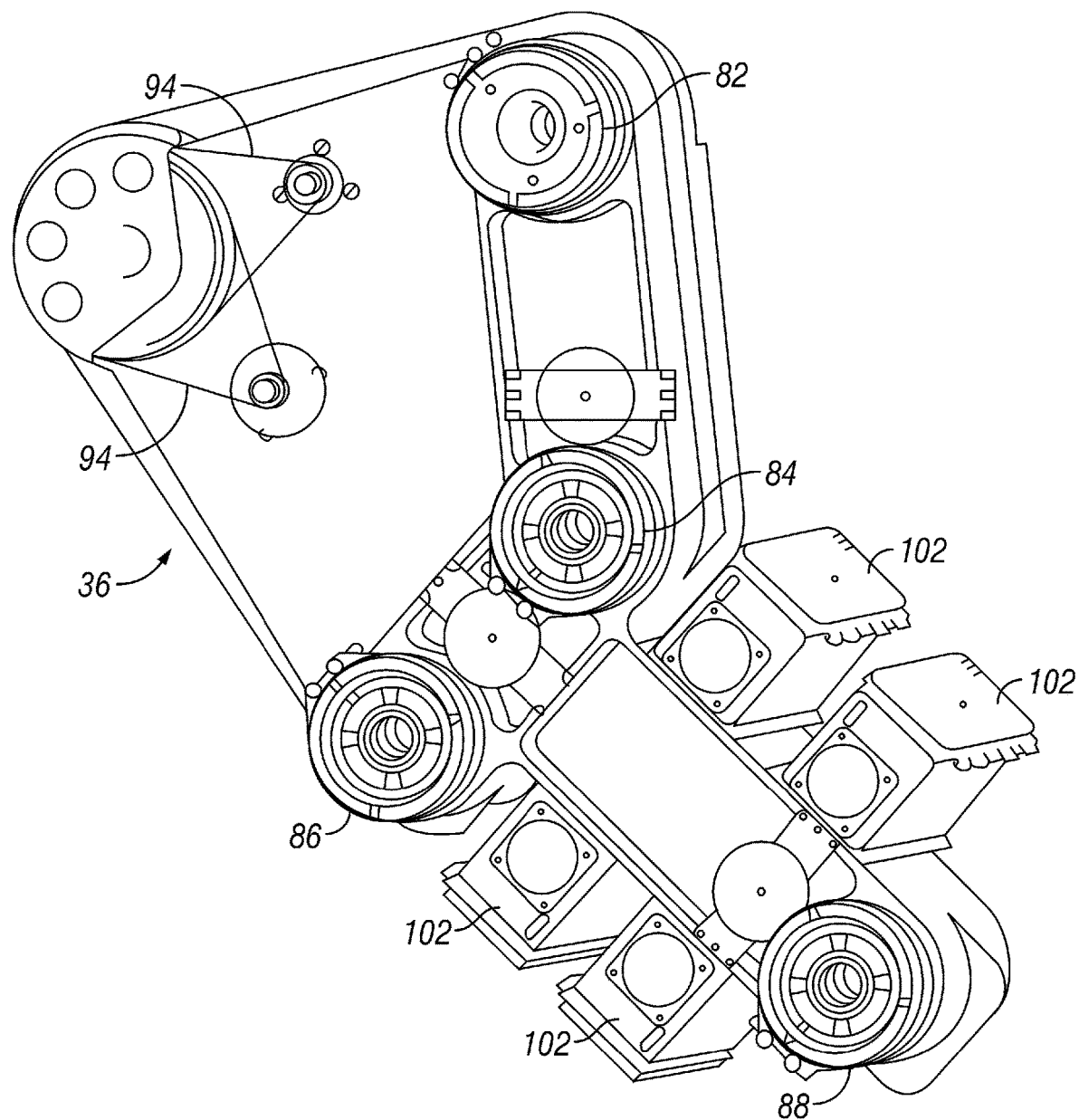
Figure 7D:
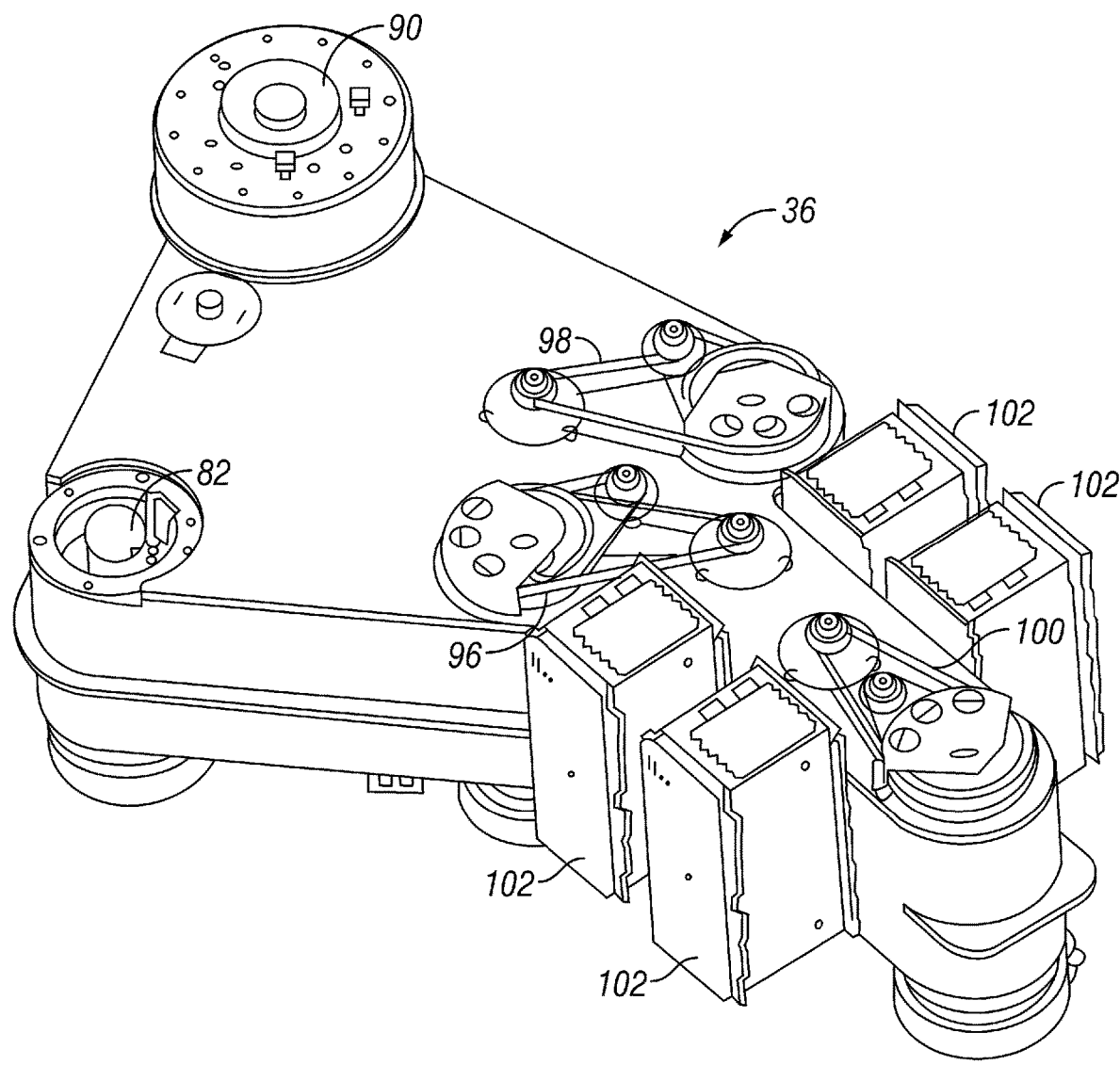

As shown in FIGS. 7A and 7D, a fifth hub 90 is coupleable to a platform linkage 92, as discussed in more detail with respect to FIGS. 8A and 8B below. The fifth hub 90 is aligned with the pivot point 78 of the set-up joint center arm 38, which is preferably coincident with its incision site for the endoscope. The fifth hub 90 provides for rotation of the orienting platform 36 about a vertical axis as denoted by arrow SJC 1 in FIG. 5A. Rotation of the orienting platform 36 about the pivot point 78 of the endoscope manipulator 34 which is aligned with the surgical incision advantageously allows for increased maneuverability of the orienting platform 36 and associated set-up arms 38, 40, 42, 44 in the direction in which a surgical procedure is to take place. This is of particular benefit during complex surgeries, as manipulator 32, 34 positioning may be varied mid-operation by simply rotating the orienting platform 36 about the fifth hub 90. Typically, the instruments will be retracted prior to rotation for safety purposes. For small rotations of the orienting platform 36 or tilting of the operating table, the low friction and balanced arms 40, 42, 44 may float while attached to the cannula during movement, pushed by force from the incisions.

Rotation of the orienting platform 36 about hub 90 (SJC 1), rotation of the set-up joint arms 40, 42 about hubs 84, 86 (SJA1 1), and rotation of the set-up joint auxiliary arm 44 about hub 88 (SJX 1) is preferably power operated, but may alternatively be manual or computer controlled. Motors driving belt and pulley mechanisms 94 for orienting platform rotation (SJC 1) are within the orienting platform as shown in FIG. 7C. A brake system may also be included to allow the orienting platform 36 to be locked into place. Motors driving belt and pulley mechanisms 96, 98, 100 for right, left, and auxiliary set-up arm rotation (SJA1 1, SJX 1) 40, 42, 44 respectively are also within the orienting platform 36 as shown in FIG. 7D. FIGS. 7C and 7D further illustrate electronic module controls 102 for each associated set-up arm 38, 40, 42, 44. The orienting platform 36 may further include a display 104, such as in interactive monitor, as shown in FIGS. 7A and 7B. This display 104 may be used for set-up purposes, instrument changes, and/or for personnel viewing of a procedure. The display 104 is preferably adjustably mounted to the orienting platform 36 with a parallelogram linkage 106 so that personnel can view the monitor in a desired direction.

Referring now to FIGS. 8A and 8B, perspective views from below and above of the platform linkage 92 for movably supporting the orienting platform 36 at hub 90 are illustrated. The platform linkage 92 generally comprises a linear rail 108, a slidable carriage 110 coupleable to the rail 108, and at least one arm 112 rotationally coupleable to the carriage 110 on a proximal end 114 and to the orienting platform 36 via hub 90 on a distal end 116. The platform linkage 92 advantageously enhances maneuverability of the modular manipulator support 30 by accommodating translation of the orienting platform 36 in three dimensions (x, y, z). Movement of the orienting platform in a generally horizontal direction is denoted by arrow OP 1. Movement of the orienting platform in a generally vertical direction is denoted by arrow OP 2. Movement of the orienting platform in and out of the page is articulated by rotational movement of joint 120, as denoted by arrow OP 3. The platform linkage 92 further accommodates rotation of the orienting platform 36 about one vertical axis, as denoted by arrow SJC 1. The arm 112 preferably comprises a four bar parallelogram linkage 118 extending between a pair of adjacent joints 120, 122. It will be appreciated that although the fifth hub 90 accommodates rotation of the orienting platform 36 (SJC 1), the system may also be designed wherein the fifth hub 90 is rotationally coupleable to the platform linkage 92 so that the platform linkage accommodates pivotal motion of the orienting platform.

The orienting platform's 36 enhanced range of motion due to the platform linkage 92 permits access to incision sites over a wide range of the patient's body. This of particular benefit when performing complicated and lengthy procedures, where the manipulators 32, 34 may be quickly repositioned mid-operation to alternative surgical sites. Typically, the instruments will be retracted prior to translation or rotation of the orienting platform 36 for safety purposes. The platform linkage 92 is preferably power operated, but may alternatively be manual or computer controlled. Motors may be located within the platform linkage 92 or orienting platform 36 to drive pulley and belt mechanisms. For example, motors driving belt and pulley mechanisms 94 with harmonic drives for orienting platform rotation about hub 90 (SJC 1) are within the orienting platform as shown in FIG. 7C. A brake system may also be included to allow the platform linkage 92 to be locked into place.

As shown in FIG. 8B, the platform linkage 92 is preferably mounted to a mounting base via bolts and brackets 124 or other conventional fastener devices. The mounting base preferably comprises a ceiling-height support structure so as to permit the manipulator support assembly 92, 30 to extend generally downward from the base. A ceiling-height mounted manipulator support assembly advantageously improves space utilization in an operating room, particularly clearing up space adjacent the operating table for personnel and/or other surgical equipment as well as minimizing robotic equipment and cabling on the floor. Further, a ceiling-height mounted manipulator support assembly minimizes the potential for collisions or space conflicts with other adjacent manipulators during a procedure and provides for convenient storage when the robotic surgery system is not in use.

The term "ceiling-height support structure" includes support structures disposed on, adjacent, or within an operating room ceiling and includes support structures disposed substantially below an actual ceiling height, especially in the case of a higher-than-typical operating room ceiling. The mounting base permits the manipulator support assembly 92, 30 to be stored by pulling it against the wall, using joints as shown in FIGS. 8A and 8B. The mounting base may include existing architectural elements, such as original or reinforced structural elements, joists, or beams. Further, the mounting base may be formed from sufficiently rigid and stiff materials to inhibit vibration. Alternatively, passive means such as viscous or elastomer dampers or active means such as servo-mechanisms may be used to counteract vibration or interfloor movement of the hospital building in vertical and/or horizontal directions.

Figure 9B:
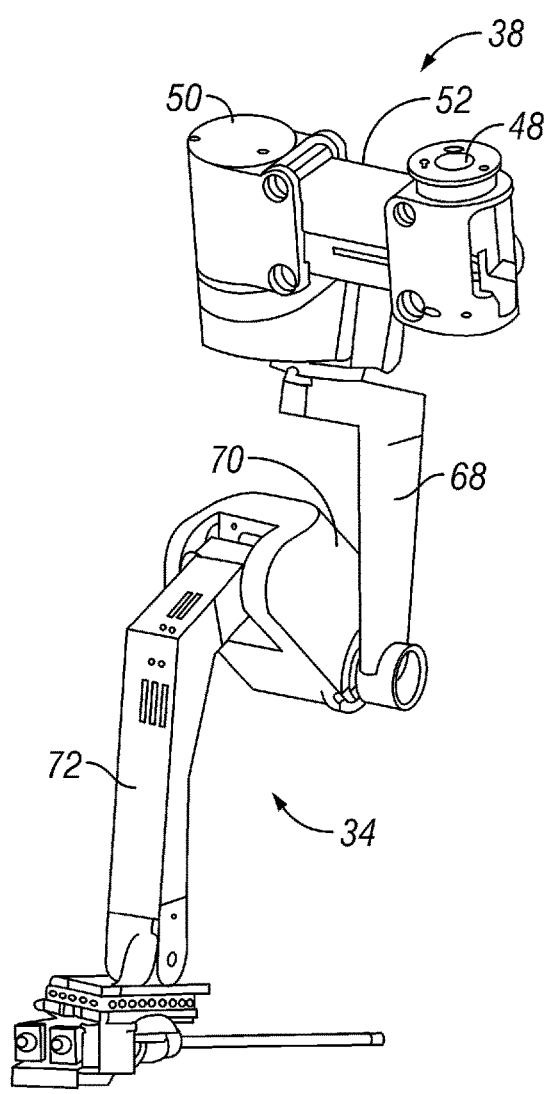
Figure 9C:
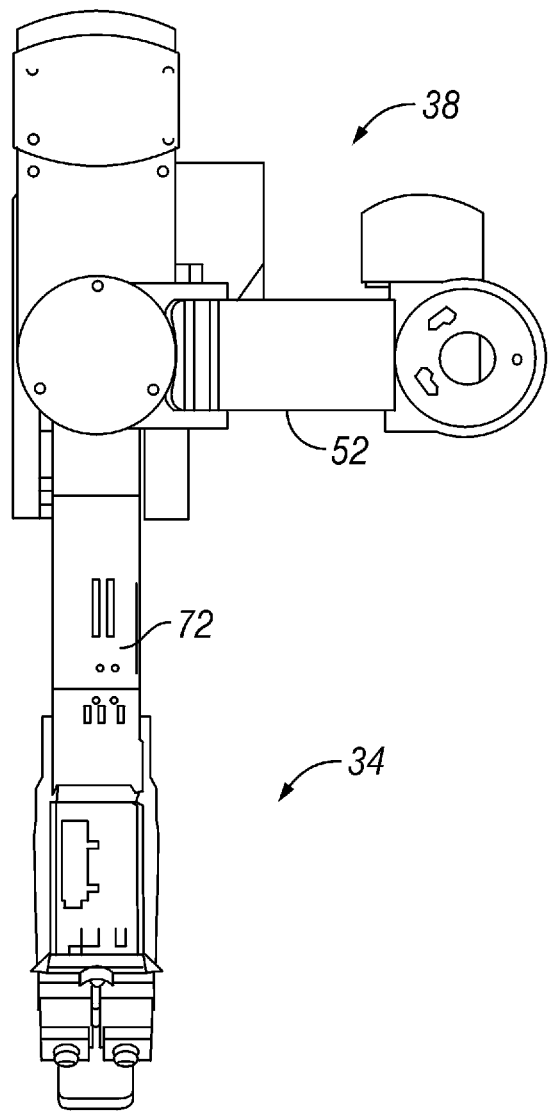
Figure 9D:
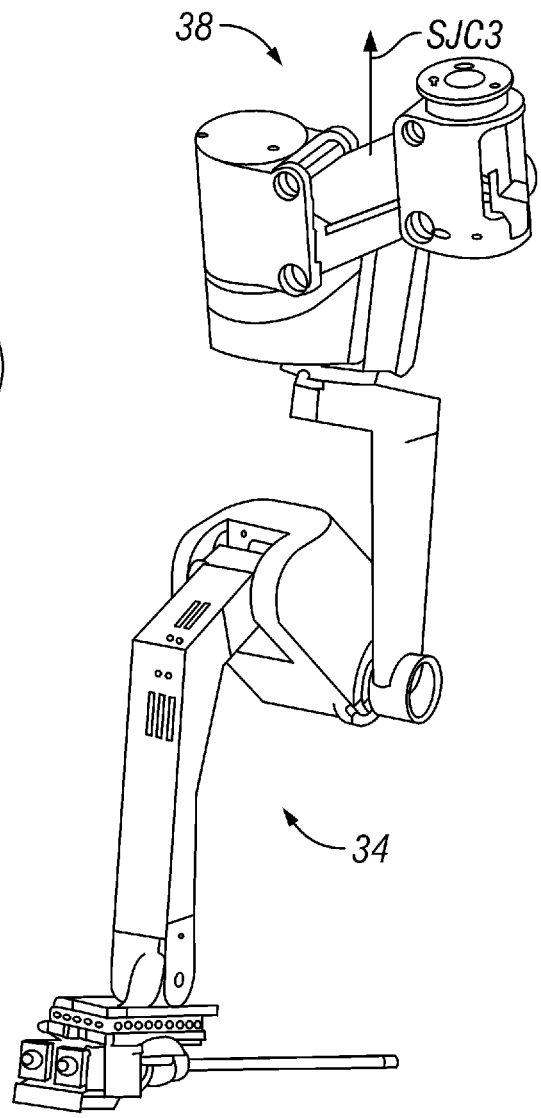
Figure 9F:
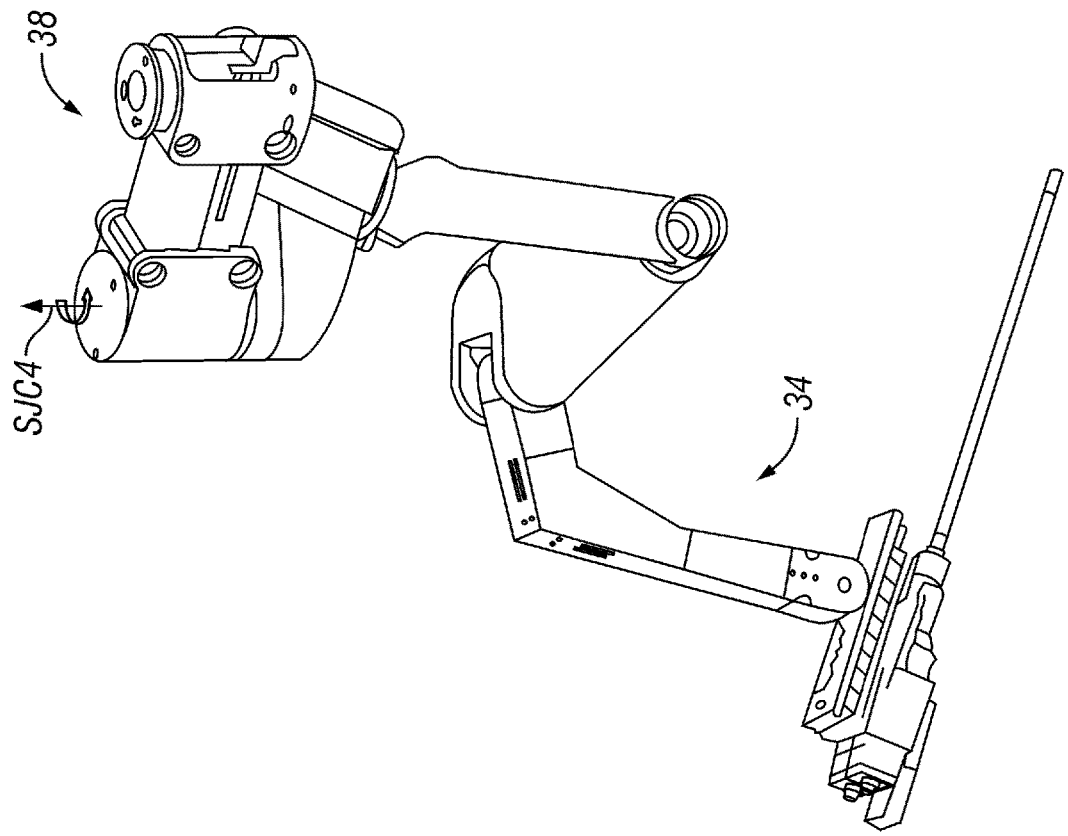
Figure 9E:
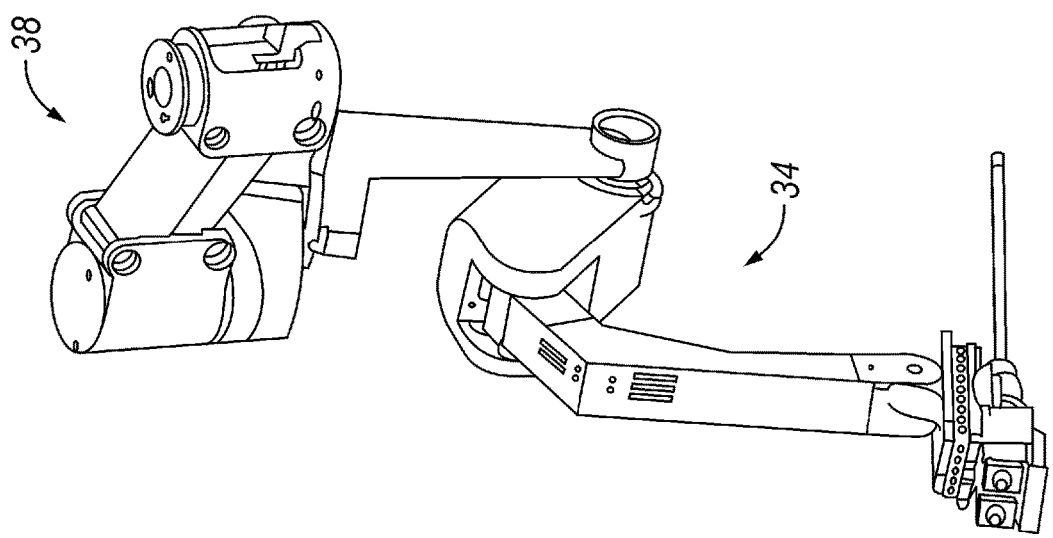

Referring now to FIGS. 9A and 9B, oblique views of the set-up joint center arm 38 supporting the endoscope camera robotic manipulator 34 are shown. FIG. 9C illustrates a top view. As discussed above, the set-up joint center arm 38 comprises a relatively short, near vertical rigid arm defined primarily by the parallelogram structure 46. The set-up joint center arm 38 has a shorter parallelogram link 52 than the other three arms 40, 42, 44. The set-up joint center arm 38 has three degrees of freedom (SJC 2, SJC 3, SJC 4) that are typically manually positioned. The set-up joint center arm 38 is free of any redundant joints as the azimuth angle is controlled by the rotation of the orienting platform 36. FIGS. 9D and 9E illustrate translation of the set-up joint center arm 38 as denoted by arrow SJC 3. FIGS. 9F and 9G illustrate rotational motion of the set-up joint center arm 38 as denoted by arrow SJC 4.

Figure 10B:
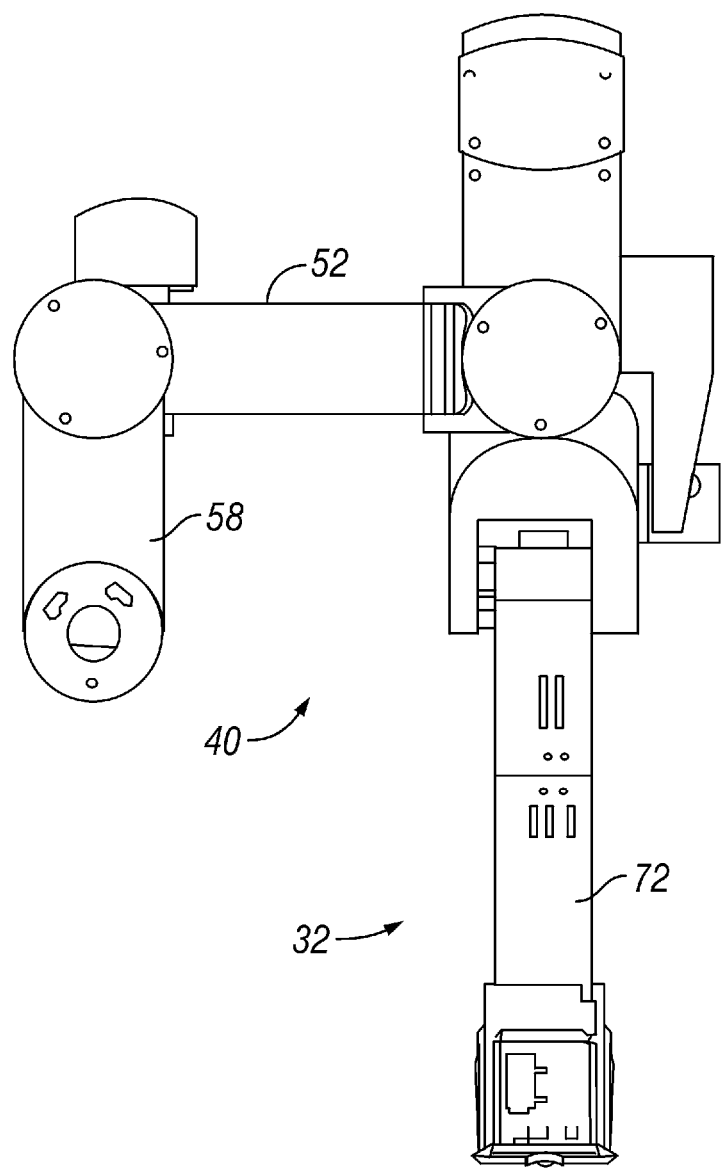
Figure 10C:
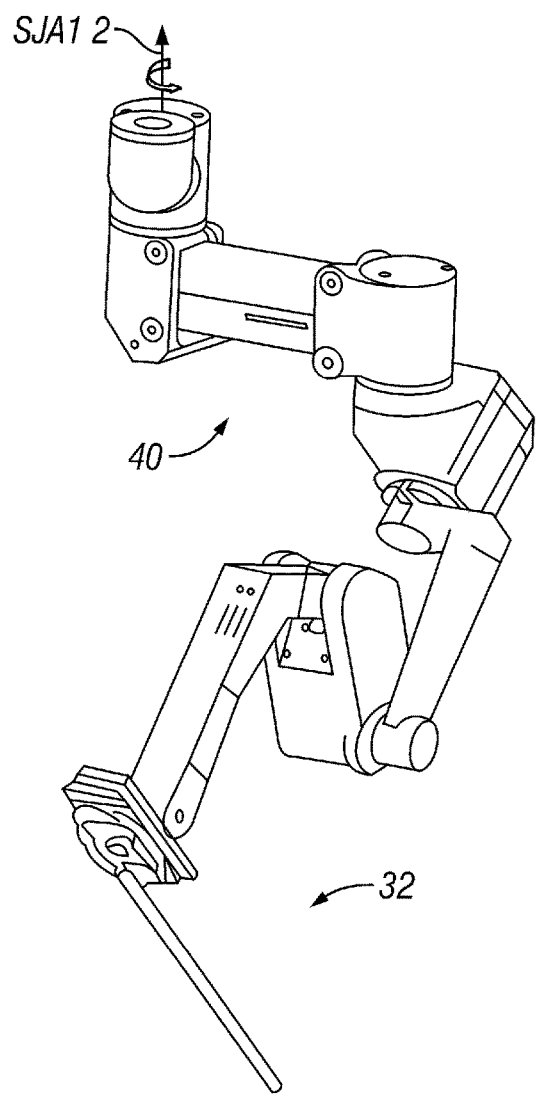
Figure 10D:
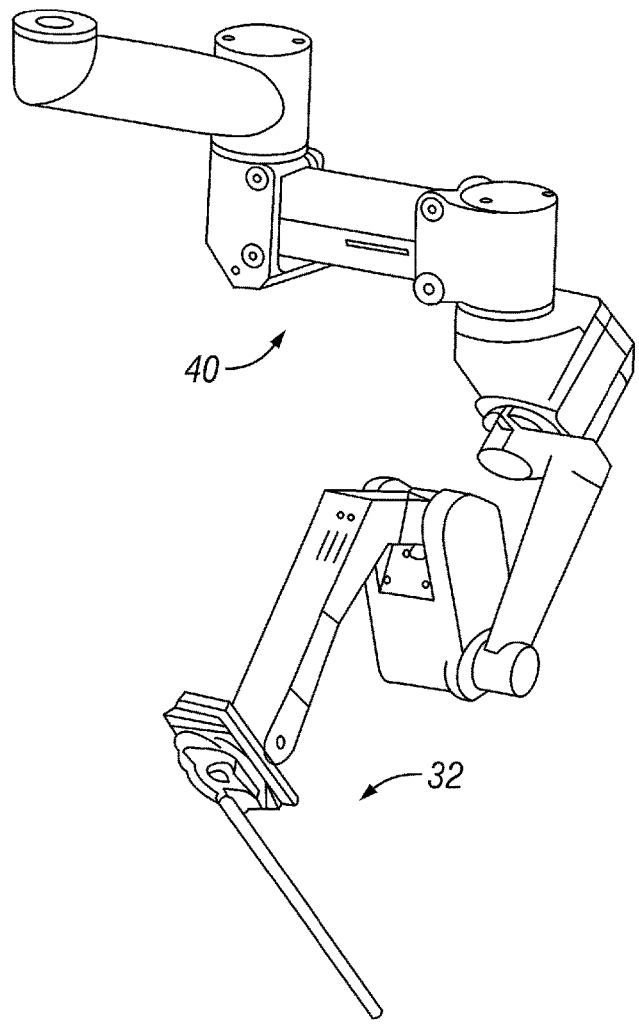
Figure 10H:
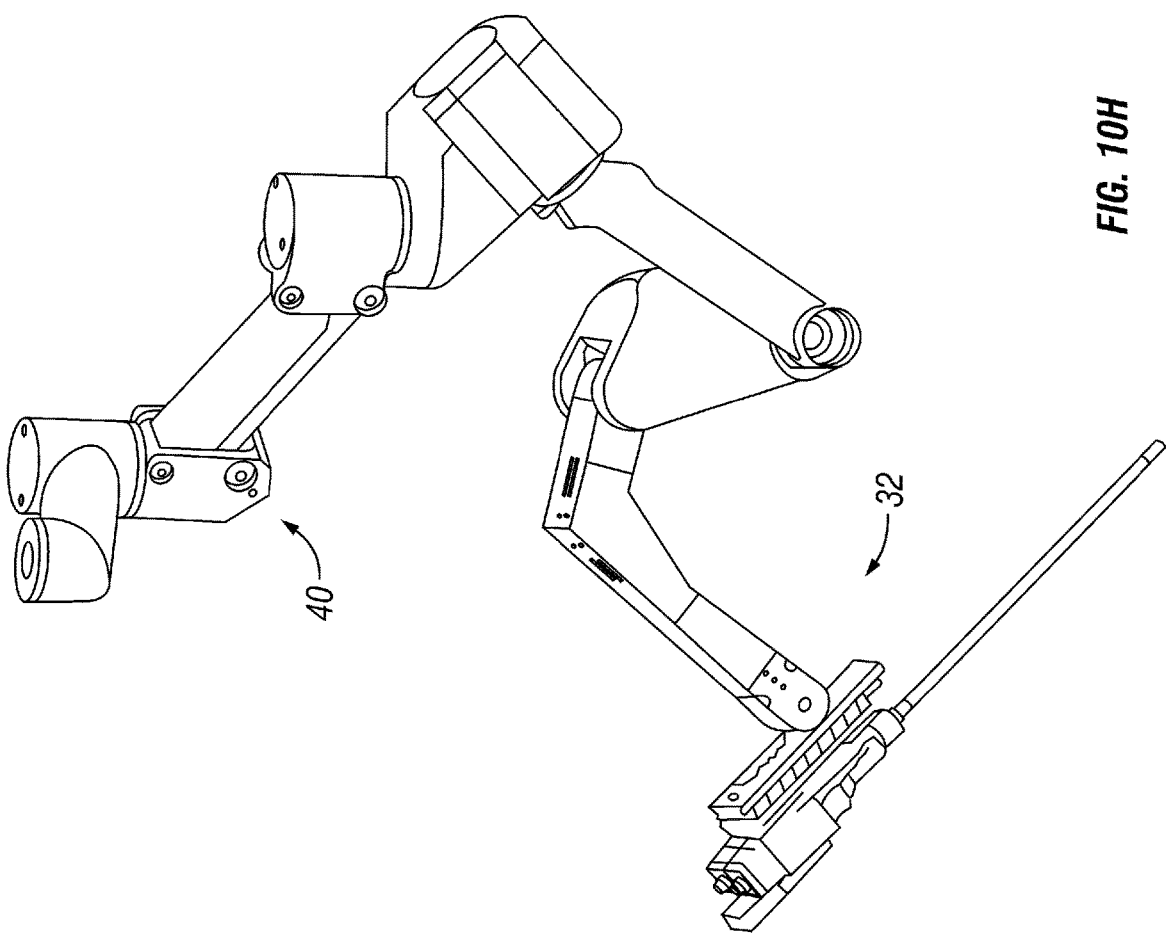
Figure 10G:
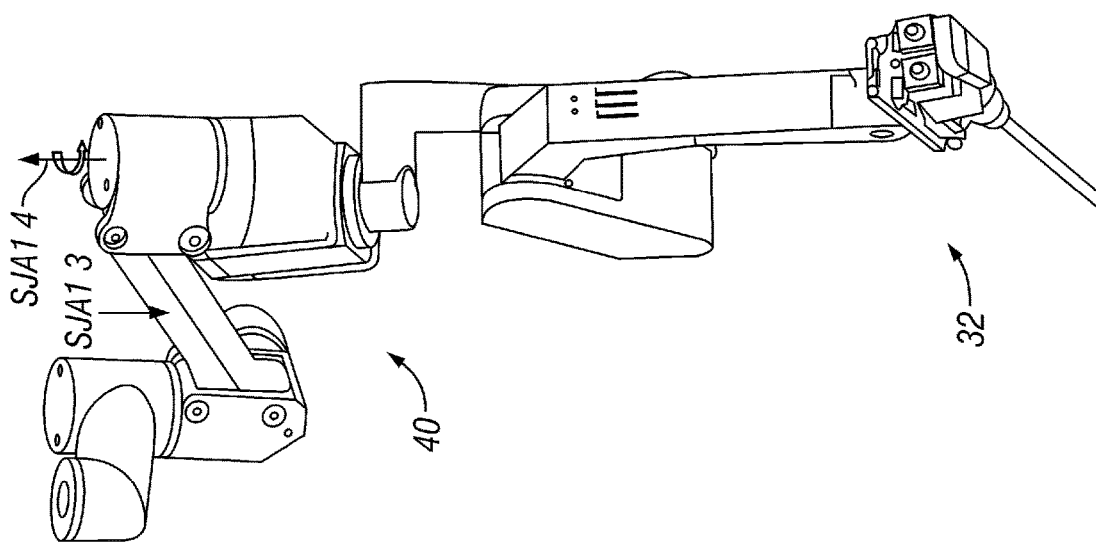

Referring now to FIGS. 10A and 10B, oblique and top views of the set-up joint arm 40 supporting the patient side robotic manipulator 32 are shown. As discussed above, the set-up joint arm 40 has four degrees of freedom (SJA1 1, SJA1 2, SJA1 3, SJA1 4), wherein the SJA1 1 joint is motorized and the other joints are manually positioned. FIGS. 10C and 10D illustrate rotational motion of the set-up joint arm 40 as denoted by arrow SJA1 2. FIGS. 10E and 10F illustrate translation of the set-up joint arm 40 as denoted by arrow SJA1 3. FIGS. 10G and 10H illustrate both translational and rotational motion of the set-up joint arm 40 as denoted by arrows SJA1 3, and SJA1 4. The translational and rotational axes for the left set-up joint arm 42 (SJA2) is identical to that of the right arm 40 (SJA1)

Figure 11B:
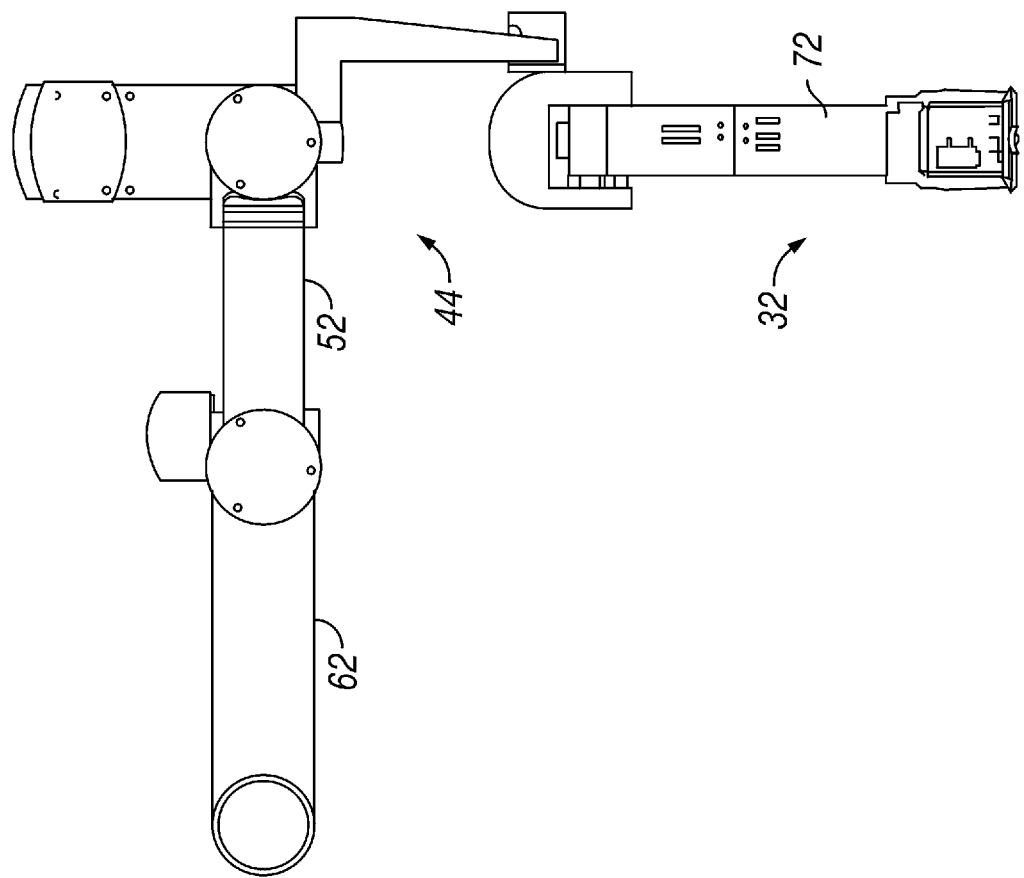
FIGS. 11A through 11D illustrate perspective and top views of the set-up joint auxiliary arm supporting and positioning a patient side robotic manipulator.
Figure 11A:
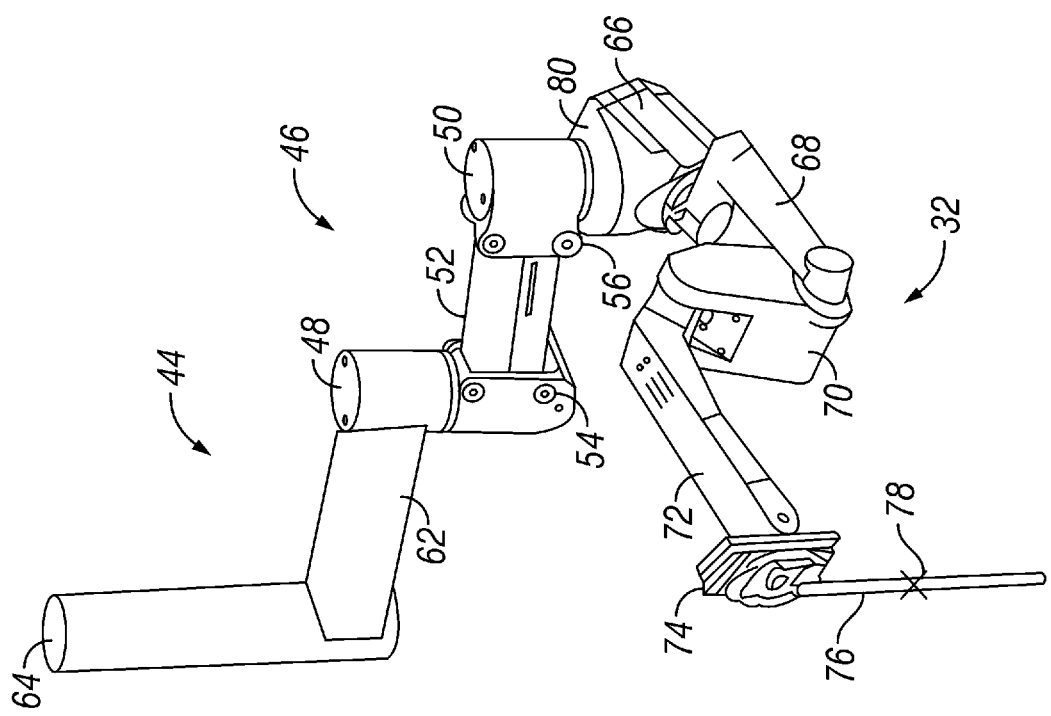
Figure 11D:
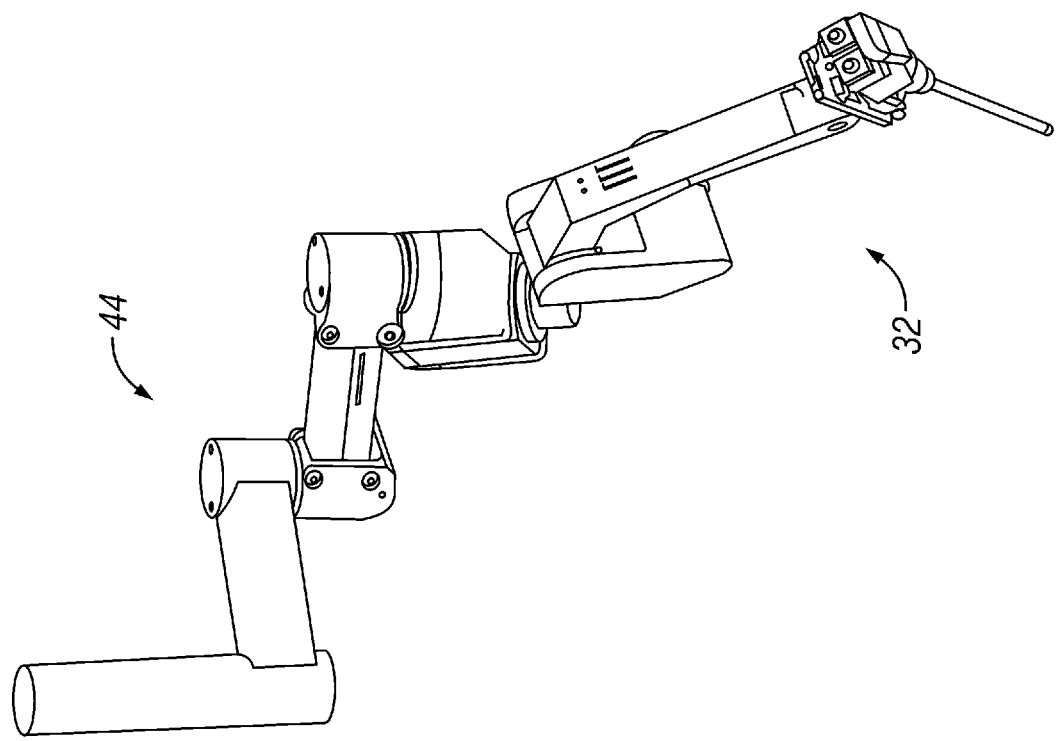
Figure 11C:
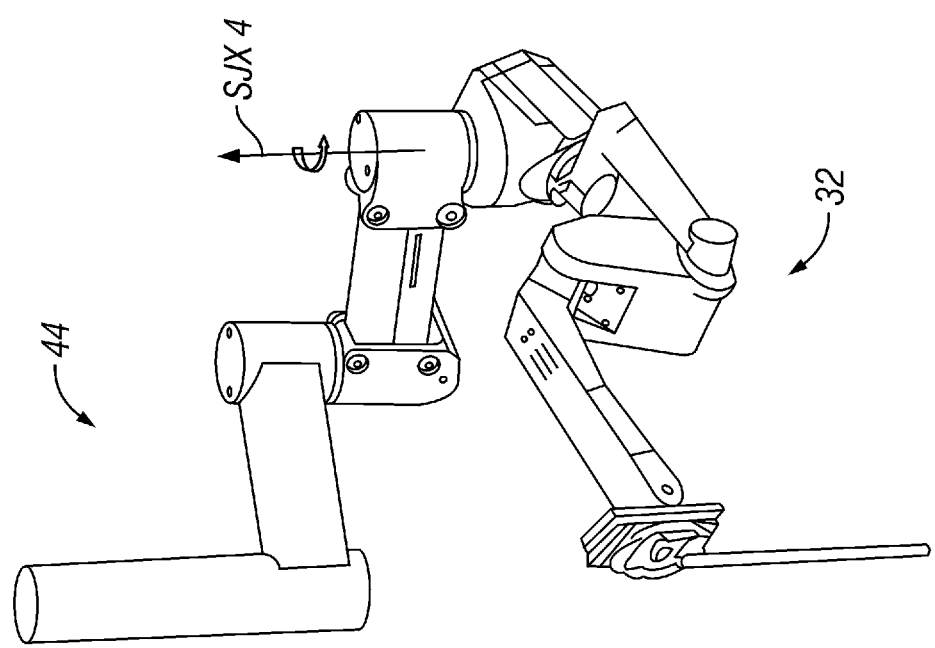

Referring now to FIGS. 11A and 11B, oblique and top views of the set-up joint auxiliary arm 44 supporting the patient side robotic manipulator 32 are shown. As discussed above, the set-up joint auxiliary arm 44 is similar in kinematics to the set-up joint arm 40, but is longer in length and has a shallower angle as its hub 88 is on an end of the orienting platform 36. The set-up joint auxiliary arm 44 has four degrees of freedom (SJX 1, SJX 2, SJX 3, SJX 4), wherein the SJX 1 joint is motorized and the other joints are manually positioned. FIGS. 11C and 11D illustrate rotational motion of the set-up joint auxiliary arm 44 as denoted by arrow SJX 4.

Figure 12B:
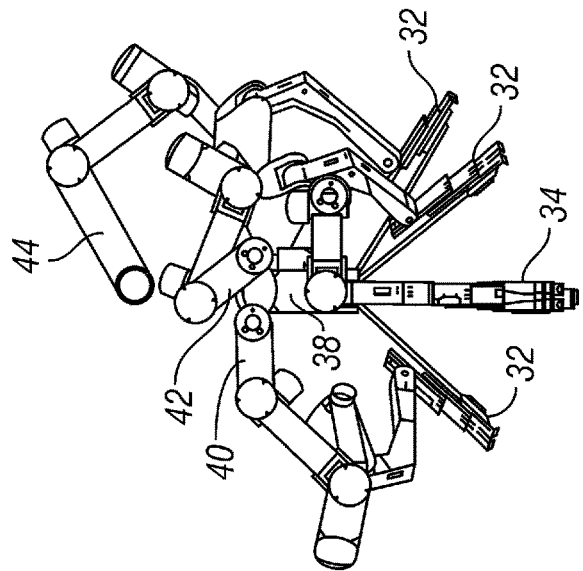
FIGS. 12A through 12C illustrate perspective views from above of four set-up joint arms showing the action of the redundant degrees of freedom.
Figure 12C:
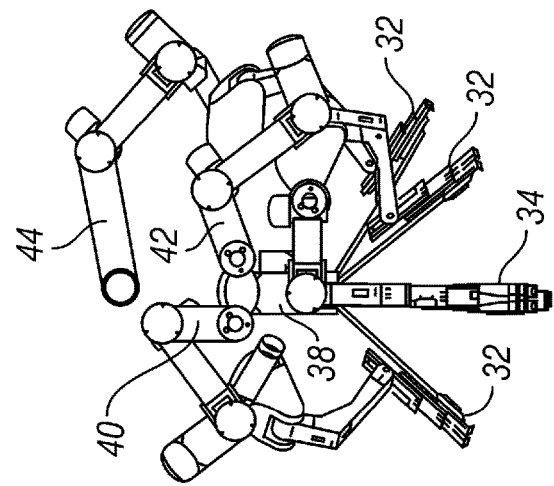
Figure 12A:
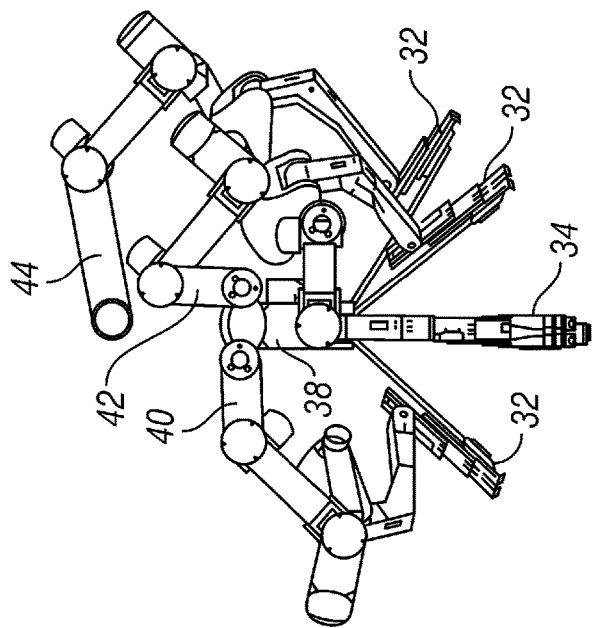

Referring now to the FIGS. 12A, 12B and 12C, perspective views from above of the four set-up joints 38, 40, 42, 44 without the orienting platform 36 are illustrated. These depictions illustrate the action of redundant degrees of freedom, altering the azimuth angle, which moves the patient side manipulator 32 farther or closer to the endoscope camera manipulator 34. In operation, once the motorized joint positions SJA1 1, SJA2 1, and SJX 1 are set, typically to preset values, the user has only to align each remote center of the patient side manipulator with each incision. This may be done by attaching each patient side manipulator to the associated cannula which is already positioned within the incision. This automatically sets the set-up joint positions, as there is no remaining redundancy. The low friction and balancing of these three joints allows the patient side manipulators to float so that each manipulator can be controlled by holding it advantageously at a single point. Setting a motorized joint to a different position will result in a different azimuth angle for the patient side manipulator after the cannula is attached. In other words, the function of the redundant, motorized joint is to allow the patient side manipulator farther from or closer to another patient side manipulator or endoscope manipulator. Alternatively, after the cannula is attached, the azimuth can be adjusted by operating the motor while the set-up joint brakes are released and the cannula is held at the incision.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A modular manipulator support for use in a robotic surgery system, the system comprising a mounting base and at least one manipulator defining driven links and joints for moving an associated instrument to manipulate tissues, the support for movably supporting and positioning the at least one manipulator relative to the base comprising:
   an orienting platform rotatably coupled to the mounting base; and
   at least one arm coupleable to the orienting platform, each of the at least one arm movably supporting an associated manipulator and defining pre-configurable and releasably fixable links and joints.

2. The modular manipulator support of claim 1, the orienting platform being linearly translatable relative to the mounting base.

3. The modular manipulator support of claim 1, the at least one arm comprising four arms, wherein the orienting platform comprises four hubs rotationally coupled to the four arms and a fifth hub coupled to the mounting base, wherein the fifth hub is aligned with a pivot point and accommodates rotation of the orienting platform about the pivot point.

4. The modular manipulator support of claim 1, wherein the at least one arm includes at least one balanced, fixable, jointed parallelogram linkage structure extending between a pair of adjacent fixable rotational joints, the jointed parallelogram linkage structure accommodating motion in a generally vertical direction, and the adjacent rotational joints accommodating pivotal motion about vertical axes.

5. The modular manipulator support of claim 1, further comprising a brake system releasably inhibiting articulation of the fixable links and joints previously configured in a substantially fixed configuration, wherein the brake system is biased toward the fixed configuration, the brake system including a brake release actuator for releasing the fixable links and joints to a repositionable configuration in which the fixable links and joints can be articulated.

6. The modular manipulator support of claim 1, further comprising a joint sensor system coupling a plurality of the fixable links and joints to a servomechanism, the joint sensor system generating joint configuration signals, wherein the servomechanism includes a computer and wherein the joint sensor system transmits the joint configuration signals to the computer.

7. The modular manipulator support of claim 1, wherein the at least one manipulator comprises an offset remote center linkage for constraining spherical pivoting of the instrument about a pivot point in space.

8. The modular manipulator support of claim 1, the at least one manipulator comprising two manipulators, the at least one arm comprising two arms.

9. A robotic surgery system comprising:
   a ceiling-height mounting base;
   an articulate support assembly movably supporting at least one surgical instrument relative to the base, the assembly comprising:
   an orienting platform coupleable to the base to permit the articulate support assembly to extend generally downward from the base;
   at least one arm coupleable to the orienting platform, each of the at least one arm defining releasably fixable links and joints that are pre-configurable; and
   at least one manipulator coupleable to the at least one arm, each of the at least one manipulator defining driven links and joints for moving the instruments so as to manipulate tissues.

10. The system of claim 9, the orienting platform being rotatably coupled to the base.

11. The system of claim 9, the orienting platform being linearly translatable relative to the base.

12. The system of claim 9, the at least one arm comprising four arms, wherein the orienting platform comprises four hubs rotationally coupled to the four arms and a fifth hub coupled to the mounting base, wherein the fifth hub is aligned with a pivot point and accommodates rotation of the orienting platform about the pivot point.

13. The system of claim 9, wherein the at least one arm includes at least one balanced, fixable, jointed parallelogram linkage structure extending between a pair of adjacent fixable rotational joints, the jointed parallelogram structure accommodating motion in a generally vertical direction, and the adjacent rotational joints accommodating pivotal motion about vertical axes.

14. The system of claim 9, further comprising a brake system releasably inhibiting articulation of the fixable links and joints previously configured in a substantially fixed configuration, wherein the brake system is biased toward the fixed configuration, the brake system including a brake release actuator for releasing the fixable links and joints to a repositionable configuration in which the fixable links and joints can be articulated.

15. The system of claim 9, further comprising a joint sensor system coupling a plurality of the fixable links and joints to a servomechanism, the sensor system generating joint configuration signals, wherein the servomechanism includes a computer and wherein the joint sensor system transmits the joint configuration signals to the computer.

16. The system of claim 9, wherein the plurality of manipulators comprises an offset remote center linkage for constraining spherical pivoting of the instrument about a pivot point in space.

* * * * *